(12) United States Patent
Takeuchi et al.

(10) Patent No.: US 8,513,220 B2
(45) Date of Patent: Aug. 20, 2013

(54) AROMATIC COMPOUNDS HAVING SPHINGOSINE-1-PHOSPHONATE (S1P) RECEPTOR ACTIVITY

(75) Inventors: Janet A. Takeuchi, Anaheim, CA (US); Ling Li, Irvine, CA (US); Xiaoxia Liu, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/569,243

(22) Filed: Aug. 8, 2012

(65) Prior Publication Data

US 2013/0018019 A1 Jan. 17, 2013

Related U.S. Application Data

(63) Continuation-in-part of application No. 13/105,590, filed on May 11, 2011, now abandoned.

(60) Provisional application No. 61/334,937, filed on May 14, 2010.

(51) Int. Cl.
| | |
|---|---|
| *A61K 31/675* | (2006.01) |
| *A61K 31/661* | (2006.01) |
| *A61K 31/662* | (2006.01) |
| *A61P 1/00* | (2006.01) |
| *A61P 9/00* | (2006.01) |
| *A61P 17/00* | (2006.01) |
| *A61P 17/06* | (2006.01) |
| *A61P 19/02* | (2006.01) |
| *A61P 25/00* | (2006.01) |
| *A61P 27/02* | (2006.01) |
| *A61P 29/00* | (2006.01) |
| *A61P 37/06* | (2006.01) |

(52) U.S. Cl.
USPC ................................ 514/89; 514/91; 514/114

(58) Field of Classification Search
None
See application file for complete search history.

(56) References Cited

U.S. PATENT DOCUMENTS 7,728,014 B2 * 6/2010 Beard et al. ............... 514/345
2008/0064872 A1 3/2008 Beard et al.

FOREIGN PATENT DOCUMENTS

| WO | 92-002513 | | 2/1992 |
| WO | 03-062248 | A2 | 7/2003 |
| WO | 2008-030838 | A2 | 3/2008 |
| WO | 2008-030843 | A1 | 3/2008 |
| WO | 2008-141013 | A1 | 11/2008 |

OTHER PUBLICATIONS

Brinkmann, 2007, Sphingosine 1-Phosphate Receptors in Health and Disease: Mechanistic Insights from Gene Deletion Studies and Reverse Pharmacology, Pharmacology & Therapeutics, 115, 84-105.
Heinrich Stahl, 2002, Pharmaceutical Salts, Handbook of Pharmaceutical Salts, -, 329-345, International Union of Pure and Applied Chemistry, Verlag Helvetica Chemica Acta-Zurich.
L.C. Cross, 1976, Rules for the Nomenclature of Organic Chemistry Section E: Sterochemistry, Pure & Appl. Chem., 45, 11-30.

\* cited by examiner

*Primary Examiner* — Janet Andreas
*Assistant Examiner* — Timothy R Rozof
(74) *Attorney, Agent, or Firm* — Doina G. Ene

(57) ABSTRACT

Novel aromatic compounds which are useful as sphingosine-1-phosphate modulators and useful for treating a wide variety of disorders associated with modulation of sphingosine-1-phosphate receptors.

8 Claims, 9 Drawing Sheets

Lymphopenia induced by S1P1 agonist Compound 2 (10mg/kg) in Mice

The number of lymphocytes found in the blood was reduced by Compound 2 after 24h of drug application.

Lymphopenia induced by S1P1 agonist Compound 3 (10mg/kg) in Mice

The number of lymphocytes found in the blood was reduced by Compound 3 after 72h of drug application.

Lymphopenia induced by S1P1 agonist Compound 4 (10mg/kg) in Mice

The number of lymphocytes found in the blood was reduced by Compound 4 after 72h of drug application.

Lymphopenia induced by S1P1 agonist Compound 5 (10mg/kg) in Mice

Cmpd 5

The number of lymphocytes found in the blood was reduced by Compound 5 after 48h of drug application.

Lymphopenia induced by S1P1 agonist Compound 6 (10mg/kg) in Mice

The number of lymphocytes found in the blood was reduced by Compound 6 after 48h of drug application.

Lymphopenia induced by S1P1 agonist <u>Compound 7</u> (10mg/kg) in Mice

Cmpd 7

The number of lymphocytes found in the blood was reduced by Compound 7 after 24h of drug application.

Lymphopenia induced by S1P1 agonist <u>Compound 9</u> (10mg/kg) in Mice

The number of lymphocytes found in the blood was reduced by Compound 9 after 48h of drug application.

Lymphopenia induced by S1P1 agonist Compound 14 (10mg/kg) in Mice for 5 hour

The number of lymphocytes found in the blood was reduced by Compound 14 after 5h of drug application.

Lymphopenia induced by S1P1 agonist Compound 16 (10mg/kg) in Mice for 5 hour

The number of lymphocytes found in the blood was reduced by Compound 16 after 5h of drug application.

AROMATIC COMPOUNDS HAVING SPHINGOSINE-1-PHOSPHONATE (S1P) RECEPTOR ACTIVITY

RELATED APPLICATIONS

This application is a Continuation-In-Part of U.S. patent application Ser. No. 13/105,590, filed May 11, 2011, which claims the benefit of U.S. Provisional Application No. 61/334,937, filed on May 14, 2010, each of which is incorporated herein by reference in its entirety.

FIELD OF THE INVENTION

The present invention relates to aromatic compounds processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Published International Patent Application No. WO 2008030843 describes heterocyclic aminophosphonates and oxyphosphonates having sphingosine-1-phosphate receptor biological activity.

Published International Patent Application No. WO 2008030838 describes heteroaromatic derivatives as sphingosine-1-phosphate receptor agonists and theft preparation and use in the treatment of diseases.

Published International Patent Application No. WO 2008141013 describes Sphingosine-1-phosphate 3 receptor inhibitors for the treatment of pain.

Published International Patent Application No. WO 9202513 describes the preparation of diphenylazines as antithrombotics vasodilators, antihypertensives, and antiinflammatories.

Granted U.S. Pat. No. 7,728,014 discloses heteroaromatic compounds having biological activity at the sphingosine-1-phosphate 3 receptor.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

Formula I

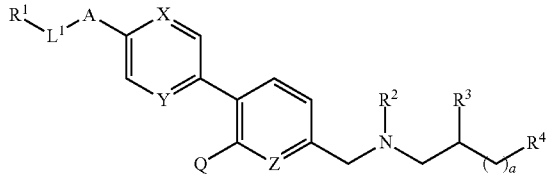

wherein:
$R^1$ is Me, $CF_3$ or aryl;
$R^2$ is H, $C_{1-10}$ alkyl, or together with $R^3$ forms a 5 or 6 membered heterocycle ring;
$R^3$ is H, $C_{1-10}$ alkyl, or together with $R^2$ forms a 5 or 6 membered heterocycle ring;
$R^4$ is $OPO_3H_2$, carboxylic acid, $C_{1-6}$ alkyl, $—S(O)_2H$, $—P(O)(OH)(OR^{10})$, $—P(O)(H)OH$ or $OR^9$;
X is $CR^5$ or N;
Y is $CR^6$ or N;
Z is $CR^7$ or N;
A is O, $CH_2$ or $NR^8$;
$L^1$ is $C_{2-10}$ alkylene;
$R^5$ is H, $C_{1-10}$ alkyl, $C_{2-6}$ alkenyl or $C_{3-10}$ cycloalkyl;
$R^6$ is H, $C_{1-10}$ alkyl, $C_{2-6}$ alkenyl or $C_{3-10}$ cycloalkyl;
$R^7$ is H, $C_{1-10}$ alkyl, $C_{2-6}$ alkenyl or $C_{3-10}$ cycloalkyl;
$R^8$ is H, $C_{3-10}$ cycloalkyl or $C_{1-6}$ alkyl;
$R^9$ is H or $C_{1-10}$ alkyl;
$R^{10}$ is H or $C_{1-10}$ alkyl;
Q is $C_{3-10}$ cycloalkyl, heterocycle or aryl; and
a is 0, 1, 2, 3 or 4.

The term "alkyl", as used herein, refers to saturated, monovalent hydrocarbon moieties having linear or branched moieties or combinations thereof and containing 1 to 10 carbon atoms. One methylene ($—CH_2—$) group, of the alkyl can be replaced by oxygen, sulfur, sulfoxide, nitrogen, carbonyl, carboxyl, sulfonyl, or by a divalent $C_{3-10}$ cycloalkyl. Alkyl groups can be substituted by halogen, hydroxyl, cycloalkyl, amino, heterocycles, carboxylic acid, phosphonic acid groups, sulphonic acid groups, phosphoric acid. Usually, in the present case, alkyl groups are methyl, n-butyl, n-propyl, hexafluoropropyl, trifluoromethyl.

The term "alkylene", as used herein, refers to saturated, divalent hydrocarbon moieties having linear or branched moieties or combinations thereof and containing 2 to 10 carbon atoms. One methylene ($—CH_2—$) group, of the alkylene can be replaced by oxygen, sulfur, sulfoxide, nitrogen, carbonyl, carboxyl, sulfonyl, or by a divalent $C_{3-10}$ cycloalkyl.

Alkylene groups can be substituted by halogen, hydroxyl, cycloalkyl, amino, heterocycles, carboxylic acid, phosphonic acid groups, sulphonic acid groups, phosphoric acid. Usually, in the present case, alkylene groups are ethylene, n-butylene, n-propylene, hexafluoropropylene.

The term "cycloalkyl", as used herein, refers to a monovalent or divalent group of 3 to 10 carbon atoms, preferably 3 to 5 carbon atoms derived from a saturated cyclic hydrocarbon. Cycloalkyl groups can be monocyclic or polycyclic. Cycloalkyl can be substituted by $C_{1-6}$ alkyl groups or halogens.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by $C_{1-6}$ alkyl, as defined above, or by halogen.

The term "halogen", as used herein, refers to an atom of chlorine, bromine, fluorine, iodine. Usually, in the present case, halogen group is fluoro.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, $C_{1-6}$ alkyl or halogens. Usually, in the present case, heterocyclic groups are pyridine, thiopene, furan, thiazol, oxazol, pyrroline, 5-fluoro-thiophen-2-yl.

The term "aryl" as used herein, refers to an organic moiety derived from an aromatic hydrocarbon consisting of a ring containing 6 to 10 carbon atoms by removal of one hydrogen, which can be substituted by halogen atoms, —$OC_{1-3}$ alkyl, $C_{1-3}$ alkyl, nitrile, $C(O)C_{1-3}$ alkyl, amino or hydroxyl groups. Usually, in the present case, aryl is phenyl, 3-fluorophenyl, 4-fluorophenyl, 3-hydroxylphenyl.

The term "hydroxyl" as used herein, represents a group of formula "—OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "nitrile", as used herein, represents a group of formula "—CN".

The term "sulfoxide" as used herein, represents a group of formula "—S(O)".

The term "carbonyl" as used herein, represents a group of formula "—C(O)".

The term "carboxyl" as used herein, represents a group of formula "—(CO)O—".

The term "sulfonyl" as used herein, represents a group of formula —$SO_2$".

The term "carboxylic acid" as used herein, represents a group of formula "—COOH".

The term "$CF_3$" as used herein, represents a trifluoromethyl group.

The term "amino" as used herein, represents a group of formula "—$NH_2$" or "—$NH(C_{1-6}$ alkyl)" or "—$N(C_{1-6}$ alkyl)($C_{1-6}$ alkyl)".

The term "phosphonic acid" as used herein, represents a group of formula "—$P(O)(OH)_2$".

The term "sulphonic acid" as used herein, represents a group of formula "—$SO_2(OH)$".

The term "phosphoric acid" as used herein, represents a group of formula "—$OP(O)(OH)_2$".

The term "Me", as used herein represents a methyl group.

Generally, $R^1$ is selected from Me, $CF_3$ or aryl. Usually $R^1$ is Me, $CF_3$, or phenyl.

Generally, $R^2$ is selected from H, $C_{1-10}$ alkyl, or together with $R^3$ forms a 5 or 6 membered heterocycle ring. Usually $R^2$ is H or form together with $R^3$ a pyrrolidine ring.

Generally, $R^3$ is selected from H, $C_{1-10}$ alkyl, or together with $R^2$ forms a 5 or 6 membered heterocycle ring. Usually $R^3$ is H or form together with $R^2$ a pyrrolidine ring.

Generally, $R^4$ is selected from $OPO_3H_2$, carboxylic acid, $C_{1-6}$ alkyl, —$S(O)_2H$, —$P(O)(OH)(O^{10})$, —$P(O)(H)OH$ or $OR^9$. Usually, $R^4$ is $P(O)(OH)(OR^{10})$.

Generally, X is $CR^5$ or N. Usually X is CH, N or C—$C_{1-6}$ alkyl.

Generally, Y is $CR^6$ or N. Usually, Y is CH or N.

Generally, Z is $CR^7$ or N. Usually, Z is CH or N.

Generally, A is O, $CH_2$ or $NR^8$. Usually, A is O or $CH_2$.

Generally, $L^1$ is $C_{2-10}$ alkylene. Usually, $L^1$ is ethylene, n-butylene, n-propylene, hexafluoropropylene.

Generally, $R^5$ is H, $C_{1-10}$ alkyl, $C_{2-6}$ alkenyl or $C_{3-10}$ cycloalkyl. Usually, $R^5$ is H or propyl.

Generally, $R^6$ is H, $C_{1-10}$ alkyl, $C_{2-6}$ alkenyl or $C_{3-10}$ cycloalkyl. Usually, $R^6$ is H.

Generally, $R^7$ is H, $C_{1-10}$ alkyl, $C_{2-6}$ alkenyl or $C_{3-10}$ cycloalkyl. Usually, $R^7$ is H.

Generally, $R^8$ is H, $C_{3-10}$ cycloalkyl or $C_{1-6}$ alkyl.

Generally, $R^9$ is H or $C_{1-10}$ alkyl.

Generally, $R^{10}$ is H or $C_{1-10}$ alkyl. Usually, $R^{10}$ is H or ethyl.

Generally, Q is $C_{3-10}$ cycloalkyl, heterocycle or aryl. Usually, Q is phenyl, pyridinyl, thiopene, oxazole, thiazole, 3-fluorophenyl, 4-fluorophenyl, 3-hydroxylphenyl, 5-fluoro-thiophen-2-yl.

Generally, a is 0, 1, 2, 3 or 4. Usually, a is 0 or 1.

In one embodiment of the invention
$R^1$ is Me, $CF_3$, phenyl; and
$R^2$ is H, or together with $R^3$ forms a 5 membered heterocycle ring; and
$R^3$ is H, or together with $R^2$ forms a 5 membered heterocycle ring; and
$R^4$ is —$P(O)(OH)(OR^{10})$; and
X is $CR^5$ or N; and
Y is $CR^6$ or N; and
Z is $CR^7$ or N; and
A is O or $CH_2$; and
$L^1$ is $C_{2-5}$ alkylene; and
$R^5$ is H or $C_{1-6}$ alkyl; and
$R^6$ is H; and
$R^7$ is H; and
$R^{10}$ is H or $C_{1-6}$ alkyl; and
Q is heterocycle or aryl; and
a is 0 or 1.

In a preferred embodiment of the invention
$R^1$ is Me or phenyl; and
$R^2$ is H; and
$R^3$ is H; and
$R^4$ is —$P(O)(OH)(OR^{10})$; and
X is $CR^5$; and
Y is $CR^6$ or N; and
Z is N; and
A is $CH_2$; and
$L^1$ is $C_{2-5}$ alkylene; and
$R^5$ is H or $C_{1-6}$ alkyl; and R⁶ is H; and
R¹⁰ is H; and
Q is heterocycle or aryl; and
a is 1.

Compounds of the invention are:
(3-{[6-(5-Hexyl-pyridin-2-yl)-biphenyl-3-ylmethyl]-amino}-propyl)-phosphonic acid;
(3-{[6-(6-Hexyl-pyridin-3-yl)-biphenyl-3-ylmethyl]-amino}-propyl)-phosphonic acid;
(3-{[5-(4-Hexyl-phenyl)-6-phenyl-pyridin-2-ylmethyl]-amino}-propyl)-phosphonic acid;
[1-(4-Hexyl-[1,1';2',1'']terphenyl-4'-ylmethyl)-pyrrolidin-3-yl]-phosphonic acid monoethyl ester;
[1-(4-Hexyl-[1,1';2',1'']terphenyl-4'-ylmethyl)-pyrrolidin-3-yl]-phosphonic acid;
(3-{[6-(6-Octyl-pyridin-3-yl)-biphenyl-3-ylmethyl]-amino}-propyl)-phosphonic acid;
(3-{[5-(4-Pentyloxy-phenyl)-6-phenyl-pyridin-2-ylmethyl]-amino}-propyl)-phosphonic acid;
(3-{[6-(4-Fluoro-phenyl)-5-(4-pentyloxy-phenyl)-pyridin-2-ylmethyl]-amino}-propyl)-phosphonic acid;
(3-{[6-(3-Fluoro-phenyl)-5-(4-pentyloxy-phenyl)-pyridin-2-ylmethyl]-amino}-propyl)-phosphonic acid;
(3-{[4-(3-Phenyl-propyl)[1,1';2',1'']terphenyl-4'-ylmethyl]-amino}-propyl)-phosphonic acid;
(3-{[4-(3,3,4,4,5,5,6,6,6-Nonafluoro-hexyl)-[1,1';2',1'']terphenyl-4'-ylmethyl]-amino}-propyl)-phosphonic acid;
(3-{[5-(4-Hexyl-3-propyl-phenyl)-6-phenyl-pyridin-2-ylmethyl]-amino}-propyl)-phosphonic acid;
(3-{[6-(3-Chloro-phenyl)-5-(4-hexyl-3-propyl-phenyl)-pyridin-2-ylmethyl]-amino}-propyl)-phosphonic acid;
[3-({6-Phenyl-5-[4-(3-phenyl-propyl)-phenyl]-pyridin-2-ylmethyl}-amino)-propyl]-phosphonic acid;
[3-({6-(3-Chloro-phenyl)-5-[4-(3-phenyl-propyl)-phenyl]-pyridin-2-ylmethyl}-amino)-propyl]-phosphonic acid;
(3-{[5-(4-Hexyl-phenyl)-6-(3-hydroxy-phenyl)-pyridin-2-ylmethyl]-amino}-propyl)-phosphonic acid;
(3-{[5-(4-Hexyl-phenyl)-6-thiophen-2-yl-pyridin-2-ylmethyl]-amino}-propyl)-phosphonic acid;
(3-{[5-(4-Hexyl-phenyl)-6-thiophen-3-yl-pyridin-2-ylmethyl]-amino}-propyl)-phosphonic acid;
(3-{[6-Furan-2-yl-5-(4-hexyl-phenyl)-pyridin-2-ylmethyl]-amino}-propyl)-phosphonic acid;
(3-{[5-(4-Hexyl-phenyl)-6-oxazol-4-yl-pyridin-2-ylmethyl]-amino}-propyl)-phosphonic acid;
(3-{[5-(4-Hexyl-phenyl)-6-thiazol-2-yl-pyridin-2-ylmethyl]-amino}-propyl)-phosphonic acid;
[3-({5-[4-(3-Phenyl-propyl)-phenyl]-6-thiophen-2-yl-pyridin-2-ylmethyl}-amino)-propyl]-phosphonic acid;
(3-{[5-(4-Hexyl-3-propyl-phenyl)-6-thiophen-2-yl-pyridin-2-ylmethyl]-amino}-propyl)-phosphonic acid;
(3-{[3-(4-Hexyl-phenyl)-[2,3']bipyridinyl-6-ylmethyl]-amino}-propyl)-phosphonic acid;
(3-{[6-(5-Fluoro-thiophen-2-yl)-5-(4-hexyl-phenyl)-pyridin-2-ylmethyl]-amino}-propylphosphonic acid.

Preferred compounds of the invention are:
(3-{[5-(4-Hexyl-3-propyl-phenyl)-6-phenyl-pyridin-2-ylmethyl]-amino}-propyl)-phosphonic acid;
[3-({6-Phenyl-5-[4-(3-phenyl-propyl)-phenyl]-pyridin-2-ylmethyl}-amino)-propyl]-phosphonic acid;
(3-{[5-(4-Hexyl-phenyl)-6-thiophen-2-yl-pyridin-2-ylmethyl]-amino}-propyl)-phosphonic acid;
(3-{[5-(4-Hexyl-phenyl)-6-thiophen-3-yl-pyridin-2-ylmethyl]-amino}-propyl)-phosphonic acid;
(3-{[6-Furan-2-yl-5-(4-hexyl-phenyl)-pyridin-2-ylmethyl]-amino}-propyl)-phosphonic acid;
(3-{[5-(4-Hexyl-phenyl)-6-oxazol-4-yl-pyridin-2-ylmethyl]-amino}-propyl)-phosphonic acid;
(3-{[5-(4-Hexyl-phenyl)-6-thiazol-2-yl-pyridin-2-ylmethyl]-amino}-propyl)-phosphonic acid;
[3-({5-[4-(3-Phenyl-propyl)-phenyl]-6-thiophen-2-yl-pyridin-2-ylmethyl}-amino)-propyl]-phosphonic acid;
(3-{[5-(4-Hexyl-3-propyl-phenyl)-6-thiophen-2-yl-pyridin-2-ylmethyl]-amino}-propyl)-phosphonic acid;
(3-{[6-(5-Fluoro-thiophen-2-yl)-5-(4-hexyl-phenyl)-pyridin-2-ylmethyl]-amino}-propyl)-phosphonic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic, for example, a hydrohalic such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermatitis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

In still another embodiment of the invention, there are provided methods for treating immunosuppressant disorders selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant rejection.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermatitis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic scheme set forth below, illustrates how compounds according to the invention can be made. Those skilled in the art will be able to routinely modify and/or adapt the following scheme to synthesize any compounds of the invention covered by Formula I.

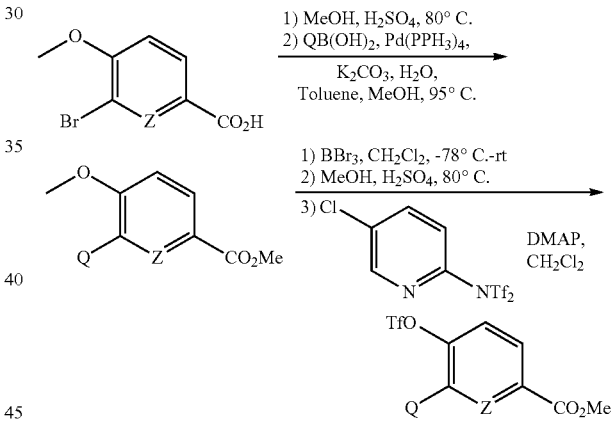

In Scheme 1, the commercially available carboxylic acid was esterified followed by a Suzuki coupling with available aryl boronic acids to give rise to the biaryl methoxy ester. Demethylation and re-esterification resulted in the corresponding phenolic ester, which was converted to a triflate.

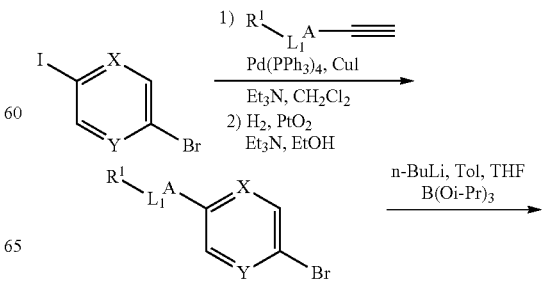

-continued

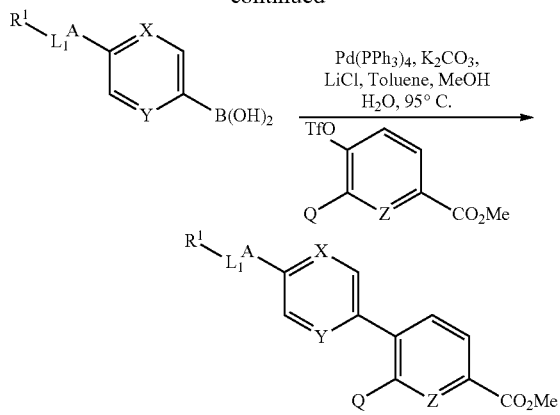

In Scheme 2, Sonogashira coupling followed by reduction of the resulting alkyne afforded the substituted aryl halide. Conversion to the boronic acid followed Suzuki coupling with the resulting aryl triflate from Scheme 1 afforded the desired triaryl ester.

Scheme 3

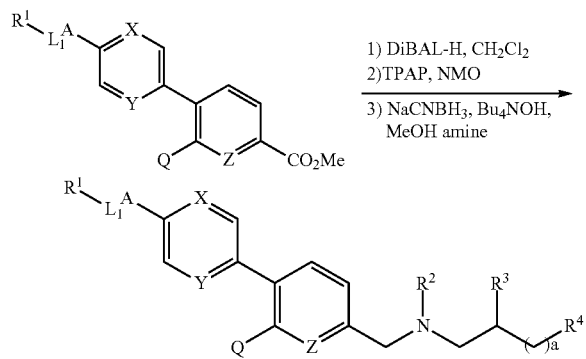

In Scheme 3, the desired final compound of Formula I, was afforded in three final steps from the triaryl ester. Reduction of the ester to the alcohol and subsequent oxidation afforded the corresponding aldehyde. Reductive amination of this aldehyde yielded the final product.

DETAILED DESCRIPTION OF THE INVENTION

Figure 1:
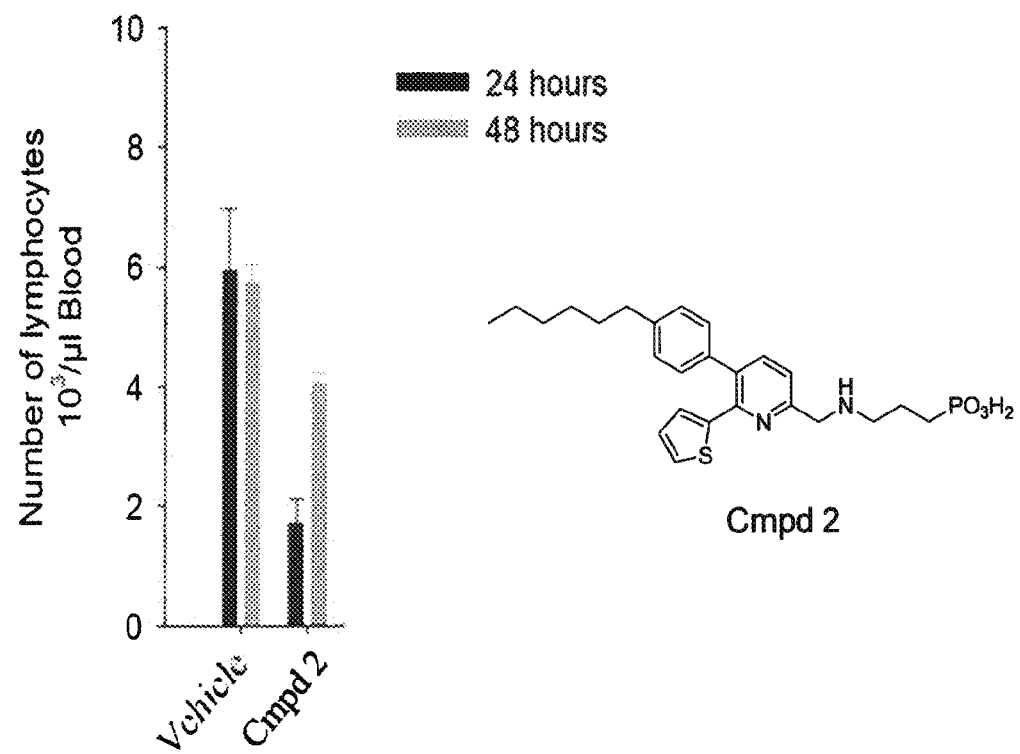
FIG. 1 shows the in vivo blood lymphocyte depletion after dosing the mice with Compound 2, (3-{[5-(4-Hexyl-phenyl)-6-thiophen-2-yl-pyridin-2-ylmethyl]-amino}-propyl)-phosphonic acid.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

The IUPAC names of the compounds mentioned in the examples were generated with ACD version 8.

Unless specified otherwise in the examples, characterization of the compounds is performed according to the following methods:

NMR spectra are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluka, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported.

The following abbreviations are used in the examples:

| | |
|---|---|
| DMF | N,N-dimethylformamide |
| NaOH | sodium hydroxide |
| $CD_3OD$ | deuterated methanol |
| HCl | hydrochloric acid |
| $CDCl_3$ | deuterated chloroform |
| DMSO-$d_6$ | deuterated dimethyl sulfoxide |
| CDI | 1,1'-carbonyldiimidazole |
| $Et_2Zn$ | diethylzinc |
| $NH_4Cl$ | ammonium chloride |
| $CH_2Cl_2$ | dichloromethane |
| $K_2CO_3$ | potassium carbonate |
| MPLC | medium pressure liquid chromatography |
| THF | tetrahydrofuran |
| $[IrCl(cod)]_2$ | di-μ-chlorobis(1,5-cyclooctadiene)diiridium(I) |
| $ClCH_2I$ | chloroiodomethane |
| RT | room temperature |
| MeOH | methanol |
| DMAP | 4-Dimethylaminopyridine |
| $MgSO_4$ | magnesium sulfate |
| LiCl | lithium chloride |
| DIBAL-H | Diisobutylaluminium hydride |
| NMO | N-Methylmorpholine-N-Oxide |
| LDA | Lithium diisopropylamide |
| MTBE | Methyl tert-butyl ether |
| $Na_2SO_4$ | sodium sulfate |
| dppp | 1,3-Bis(diphenylphosphino)propane |

Those skilled in the art will be able to routinely modify and/or adapt the following schemes to synthesize any compound of the invention covered by Formula I.

Some compounds of this invention can generally be prepared in one step from commercially available literature starting materials.

Example 1

Intermediate 1

Methyl 6-methoxybiphenyl-3-carboxylate

To a solution of methyl 3-bromo-4-methoxybenzoate (13 g, 53 mmol) in toluene (500 mL), methanol (65 mL), and water (106 mL) was added phenyl boronic acid (7.8 g, 63.6 mmol) and potassium carbonate (14.6 g, 106 mmol) and bubbled with argon for 6 min. Tetrakis(triphenylphosphine) palladium(0) (370 mg) was added and bubbled with argon for another 2 min. The reaction mixture was then heated to 95° C. for 20 h with stirring. After cooling to RT, the two phases were separated and the aqueous layer was extracted with ether, dried with magnesium sulfate, and concentrated. Purification by MPLC (5% ethyl acetate in hexanes) gave 12.2 g of the desired product as an off white solid.

Example 2

Intermediate 2

Methyl 6-{[(trifluoromethyl)sulfonyl]oxy}biphenyl-3-carboxylate

To a solution of Intermediate 1 (12.2 g, 50.4 mmol) in dichloromethane (200 mL) at −78° C. was added boron tribromide (100 mL, 1M in dichloromethane) dropwise with stirring. The reaction mixture was warmed to RT and stirred for 16 h, after which time, the reaction mixture was cooled to −78° C. and boron tribromide (20 mL, 1M in dichloromethane) was added and stirred at RT for another 6 h. Cooling to −10° C., the reaction mixture was quenched with a saturated solution of sodium bicarbonate. The layers were separated and the aqueous layer was acidified with 1N HCl. Extraction of the aqueous layer with ethyl acetate followed by combination of the organic layers, washed with brine, dried with magnesium sulfate, and concentrated to afford 6 g corresponding phenolic acid as colorless foam.

A solution of the resulting carboxylic acid (6 g, 26.3 mmol) in MeOH (80 mL) was added and fuming sulfuric acid (3 mL) dropwise. After heating to 80° C. for 16 h, the reaction mixture was cooled to RT and concentrated under reduced pressure. The residue was diluted with water and extracted with ethyl acetate, dried over magnesium sulfate and concentrated under reduced pressure to give 5.17 g desired phenolic ester.

To a solution of the resulting phenolic ester (5.17 g, 22.6 mmol) in dichloromethane (500 mL) was added N-(5-chloro-2-pyridyl)bis(trifluoromethanesulfonimide) (13.3 g, 34 mmol) and DMAP (5.5 g, 45.2 mmol) with stirring. After 16 h at RT, the reaction mixture was quenched with water. The aqueous layer was extracted with ethyl acetate, dried ($MgSO_4$), and concentrated under reduced pressure. Purification by MPLC (5% ethyl acetate in hexanes) gave rise to 6.67 g of the title compound as a colorless oil.

$^1$H NMR (300 MHz, $CDCl_3$) δ 8.19 (d, J=2.05 Hz, 1H), 8.11 (dd, J=2.20, 8.64 Hz, 1H), 7.46-7.50 (m, 6H), 3.96 (s, 3H).

Example 3

Intermediate 3

Methyl 4-hexyl-1,1',2',1''-terphenyl-4'-carboxylate

To a solution of aryl bromide (2.8 g, 11.6 mmol) in THF (100 mL) at −78° C. was added t-butyllithium (1.7 M in pentane, 13.8 mL) slowly dropwise. After stirring at −78° C. for 1 h, trimethyl borate (2.63 mL, 23.56 mmol) was added. The reaction mixture was warmed to RT over 2 h. After stirring at RT for 15 min, the reaction mixture was quenched with saturated solution of ammonium chloride and extracted with ethyl acetate. The combined organic layers were washed with HCl (10% solution), brine, and dried ($MgSO_4$), filtered, and concentrated under reduce pressure to give 2.22 g boronic acid.

A solution of the resulting boronic acid (2.22 g) and Intermediate 2 (3.8 g, 10.7 mmol) in toluene (200 mL) were added potassium carbonate (2.95 g, 21.4 mmol) and LiCl (454 mg) with stirring. After bubbling with Ar for 10 min, tetrakis(triphenylphosphine) palladium(0) (370 mg) was added and heated to 95° C. for 16 h. After the reaction mixture was cooled to RT, it was diluted with water and extracted with ethyl acetate. The combined organic layers were washed with brine, and dried ($MgSO_4$), filtered, and concentrated under reduce pressure. The residue was purified by MPLC (0-10% ethyl acetate in hexanes) gave 2.32 g of ester as a colorless oil.

¹H NMR (300 MHz, CDCl₃) δ 8.09 (d, J=1.76 Hz, 1H), 8.05 (dd, J=1.76, 7.91 Hz, 1H), 7.50 (d, J=7.91 Hz, 1H), 7.20-7.24 (m, 3H), 7.13-7.17 (m, 2H), 7.04 (s, 4H), 3.94 (s, 3H), 2.56 (t, J=7.62 Hz, 2H), 1.53-1.63 (m, 2H), 1.25-1.33 (m, 6H), 0.88 (t, J=6.45 Hz, 3H)

Intermediates 4-8 were prepared from Intermediate 2 and the corresponding aryl bromide derivatives, in a similar manner to the method described in Example 3 for Intermediate 3. The results are described below in Table 1.

TABLE 1

| Interm. number | IUPAC name | ¹H NMR δ (ppm) for Intermediate |
|---|---|---|
| 4 | Methyl-4-octyl-1,1': 2',1"-terphenyl-4'-carboxylate | ¹H NMR (300 MHz, CDCl₃) δ 8.10 (d, J = 1.76 Hz, 1H), 8.05 (dd, J = 1.76, 7.91 Hz, 1H), 7.49 (d, J = 7.91 Hz, 1H), 7.20-7.25 (m, 3H), 7.12-7.17 (m, 3H), 7.03 (s, 4H), 3.94 (s, 3H), 2.52-2.58 (m, 2H), 1.53-1.62 (m, 2H), 1.28 (d, J = 5.57 Hz, 10H), 0.88 (t, J = 6.45 Hz, 3H) |
| 5 | Methyl-6-(6-hexylpyridin-3-yl)biphenyl-3-carboxylate | ¹H NMR (300 MHz, CDCl₃) δ 8.34-8.40 (m, J = 0.59, 2.34 Hz, 1H), 8.12 (d, J = 1.47 Hz, 1H), 8.09 (dd, J = 1.76, 7.91 Hz, 1H), 7.49 (d, J = 7.91 Hz, 2H), 7.11-7.29 (m, 5H), 6.97 (d, J = 8.20 Hz, 1H), 3.95 (s, 3H), 2.75 (t, J = 7.62 Hz, 2H), 1.64-1.74 (m, 2H), 1.26-1.36 (m, 6H), 0.87 (t, J = 6.74 Hz, 3H) |
| 6 | Methyl-6-(6-octylpyridin-3-yl)biphenyl-3-carboxylate | ¹H NMR (300 MHz, CDCl₃) δ 8.37 (dd, J = 0.88, 2.34 Hz, 3H), 8.08-8.13 (m, 2H), 7.49 (d, J = 7.91 Hz, 1H), 7.22-7.29 (m, 4H), 7.12-7.15 (m, 2H), 6.97 (dd, J = 0.59, 7.91 Hz, 1H), 3.95 (s, 3H), 2.74 (dd, J = 7.60 Hz, 2H), 1.64-1.74 (m, 2H), 1.23-1.35 (m, 10H), 0.88 (t, J = 6.45 Hz, 3H) |
| 7 | Methyl-4-(3,3,4,4,5,5,6,6,6-nonafluorohexyl)-1,1': 2',1"-terphenyl-4'-carboxylate | ¹H NMR (300 MHz, CDCl₃) δ 8.04-8.11 (m, 2H), 7.48 (d, J = 7.91 Hz, 2H), 7.21-7.25 (m, 3H), 7.11-7.17 (m, 2H), 7.09 (s, 3H), 3.94 (s, 3H), 2.85-2.91 (m, 2H), 2.26-2.44 (m, 2H) |
| 8 | Methyl-4-(3-phenylpropyl)-1,1': 2',1"-terphenyl-4'-carboxylate | ¹H NMR (300 MHz, CDCl₃) δ 8.10 (d, J = 1.47 Hz, 1H), 8.05 (dd, J = 1.76, 7.91 Hz, 1H), 7.46-7.51 (m, 2H), 7.13-7.31 (m, 9H), 7.04 (s, 4H), 3.94 (s, 3H), 2.61 (t, J = 7.62 Hz, 4H), 1.88-1.98 (m, 2H) |

Example 4

Intermediate 9

Ethyl 6-(2-furyl)-5-(4-hexylphenyl)pyridine-2-carboxylate

To a solution of methyl 3-propyl-4-{[(trifluoromethyl)sulfonyl]oxy}benzoate (2.09 g, 7.11 mmol) and 1-hexyne (1.12 mL) in DMF (17.5 mL) and triethyl amine (3.5 mL) was added dppp (100 mg, 0.14 mmol). After heating to 95° C. with stirring for 16 h, the reaction mixture was cooled to RT, diluted with diethyl ether and washed with water. The ethereal layer was washed with brine, and dried (MgSO₄), filtered, and concentrated under reduce pressure. The residue was purified by MPLC (3% ethyl acetate in hexanes) to give 11.9 g ethyl 6-(2-furyl)-5-(4-hexylphenyl)pyridine-2-carboxylate as a brown oil.

¹H NMR (300 MHz, CDCl₃) δ 7.84 (d, J=1.76 Hz, 1H), 7.77 (dd, J=1.61, 8.06 Hz, 1H), 7.41 (d, J=7.91 Hz, 1H), 3.90 (s, 3H), 2.77 (t, J=7.91 Hz, 2H), 2.47 (t, J=6.70 Hz, 2H), 1.44-1.74 (m, 6H), 0.96 (t, J=7.33 Hz, 6H).

Example 5

Intermediate 10

Methyl 4-hexyl-3-propylbenzoate

To a solution of Intermediate 9 (2.5 g, 9.7 mmol) in ethanol (110 mL) was added palladium hydroxide on carbon (20% wt on carbon, 700 mg). After stirring at RT under hydrogen balloon atmosphere for 16 h, the reaction mixture was filtered through celite and concentrated under reduced pressure. Filtration through a short plug of silica gel afforded 4.7 g of methyl 4-hexyl-3-propylbenzoate as a brown oil.

¹H NMR (300 MHz, CDCl₃) δ 7.82 (d, J=1.47 Hz, 1H), 7.78 (dd, J=1.76, 7.91 Hz, 1H), 7.20 (d, J=7.91 Hz, 1H), 3.89 (s, 3H), 2.59-2.67 (m, 4H), 1.52-1.69 (m, 4H), 1.22-1.41 (m, 6H), 0.99 (t, J=7.33 Hz, 3H), 0.89 (t, J=6.45 Hz, 3H)

Example 6

Intermediate 11

(4-hexyl-3-propylphenyl)methanol

To a solution of Intermediate 10 6.4 g, 24.4 mmol) in dichloromethane (230 mL) at −78° C. was added DIBAL-H (1.0 M in dichloromethane, 58.6 mL, 58.6 mmol). The reaction was warmed to RT over for 20 h with stirring and was quenched at −10° C. with methanol and 10% solution of HCl. The mixture was diluted with water and the aqueous layer was extracted with ethyl acetate. The combined organic layers were washed with brine, dried over MgSO₄, and concentrated under reduced pressure to afford 5.4 g of (4-hexyl-3-propylphenyl)methanol as a yellow oil.

¹H NMR (300 MHz, CDCl₃) δ 7.11-7.18 (m, 3H), 4.63 (s, 2H), 2.59 (td, J=1.32, 7.84 Hz, 4H), 1.50-1.68 (m, 4H), 1.22-1.40 (m, 6H), 0.99 (t, J=7.33 Hz, 3H), 0.89 (t, J=6.74 Hz, 3H)

Example 7

Intermediate 12

4-hexyl-3-propylbenzaldehyde

To a solution of Intermediate 11 (4.1 g, 17.5 mmol), NMO (5.1 g, 43 mmol), and 4 A molecular sieves (4 g) in dichloromethane (170 mL) and acetonitrile (22 mL) was added tetrapropylammonium perruthenate (TPAP, 320 mg). After stirring at RT for 2 h, the reaction mixture was filtered through a short column of silica gel, eluted with ethyl acetate and concentrated under reduced pressure. Purification by MPLC (0-20% ethyl acetate in hexanes) gave rise to 2.96 g 4-hexyl-3-propylbenzaldehyde as a yellow oil.

$^1$H NMR (300 MHz, CDCl$_3$) δ 9.95 (s, 1H), 7.66 (d, J=1.47 Hz, 1H), 7.63 (dd, J=1.80, 7.62 Hz, 1H), 7.30 (d, J=7.62 Hz, 1H), 2.63-2.70 (m, 4H), 1.54-1.71 (m, 4H), 1.26-1.43 (m, 6H), 1.00 (t, J=7.33 Hz, 3H), 0.90 (t, J=6.70 Hz, 3H)

Example 8

Intermediate 13

(2E)-3-(4-hexyl-3-propylphenyl)acrylaldehyde

To a solution of LDA (1.5M in cyclohexane, 9 mL, 13.5 mmol) in THF (28 mL) at 0° C., was added a solution of 2-methyl-N-[2-(triethylsilyl)ethylidene]-2-propanamine (2.9 g, 13.5 mmol) in THF (6 mL) dropwise and stirred for 30 min. The reaction mixture was cooled to −78° C. and a solution of Intermediate 12 (2.6 g, 12.3 mmol) in THF (6 mL) was added dropwise. After warming to RT over 3.5 h, the reaction mixture was quenched with citric acid (20% solution, 40 mL) and stirred for another 16 h. The mixture was washed with brine, extracted with diethyl ether, dried over MgSO$_4$, and concentrated under reduced pressure. Purification of the crude product by MPLC (10% ethyl acetate in hexanes) afforded 3.8 g (2E)-3-(4-hexyl-3-propylphenyl)acrylaldehyde $^1$H NMR (300 MHz, CDCl$_3$) δ 9.68 (d, J=7.91 Hz, 1H), 7.44 (d, J=16.12 Hz, 1H), 7.31-7.36 (m, 2H), 7.20 (d, J=8.50 Hz, 1H), 6.69 (dd, J=7.62, 15.82 Hz, 1H), 2.59-2.66 (m, 4H), 1.52-1.69 (m, 4H), 1.28-1.43 (m, 6H), 1.00 (t, J=7.33 Hz, 3H), 0.90 (t, J=6.74 Hz, 3H)

Example 9

Intermediate 14

(2E)-3-[4-(3-phenylpropyl)phenyl]acrylaldehyde

To a solution of 1-bromo-4-(3-phenylpropyl)-benzene (684 mg, 2.48 mmol) in DMF (10 mL) were added acrolein diethyl acetal (1.7 mL, 11.1 mmol), tetrabutylammonium acetate (1.87 g, 6.2 mmol), potassium carbonate (514 mg, 3.72 mmol), potassium chloride (185 mg, 2.48 mmol), and palladium(II) acetate (50 mg, 0.22 mmol). After stirring at 90° C. for 4 h, the reaction mixture was cooled to RT and HCl (2M, 15 mL) was added. After stirring for 10 min at RT, the mixture was extracted with MTBE and washed with water and brine, dried over MgSO$_4$ and concentrated under reduced pressure. Purification by MPLC (20% ethyl acetate in hexanes) gave 390 mg (2E)-3-[4-(3-phenylpropyl)phenyl]acrylaldehyde as a yellow oil.

$^1$H NMR (300 MHz, CDCl$_3$) δ 9.69 (d, J=7.62 Hz, 1H), 7.42-7.51 (m, 3H), 7.16-7.32 (m, 7H), 6.69 (dd, J=7.62, 15.82 Hz, 1H), 2.67 (q, J=8.20 Hz, 4H), 1.91-2.03 (m, 2H)

Example 10

Intermediate 15 ethyl (2Z,4E)-2-azido-5-(4-hexyl-3-propylphenyl)penta-2,4-dienoate

To a freshly prepared solution of sodium ethoxide (76 mmol) at −10° C. was added a solution of ethyl azidoacetate (25% in ethanol, 39.2 mL, 76 mmol) followed by a solution of Intermediate 13 (3.25 g, 12.6 ml) in ethanol (45 mL). After stirring for 1 h at −10° C., the reaction mixture was quenched with water and brine and extracted with ethyl acetate. The combined organic layers were washed with water and brine, dried over MgSO4, and concentrated under reduced pressure. Purification by MPLC (10% ethyl acetate in hexanes) gave rise to 1.65 g ethyl (2Z,4E)-2-azido-5-(4-hexyl-3-propylphenyl)penta-2,4-dienoate as a yellow oil.

$^1$H NMR (300 MHz, CDCl$_3$) δ 7.23-7.26 (m, 2H), 7.11 (s, 2H), 6.73-6.81 (m, 2H), 4.33 (q, J=7.13 Hz, 2H), 2.59 (t, J=7.91 Hz, 2H), 2.59 (t, J=7.91 Hz, 2H), 1.51-1.68 (m, 4H), 1.37 (t, J=7.18 Hz, 3H), 1.24-1.43 (m, 6H), 1.00 (t, J=7.33 Hz, 3H), 0.90 (t, J=7.00 Hz, 3H).

Intermediates 16-18 were prepared from the corresponding starting materials, in a similar manner to the method described in Example 10 for Intermediate 15. The starting materials used and the results are described below in Table 2.

TABLE 2

| Interm. number | IUPAC name | Starting Materials | $^1$H NMR δ (ppm) for Intermediate |
| --- | --- | --- | --- |
| 16 | ethyl (2Z,4E)-2-azido-5-(4-hexylphenyl)penta-2,4-dienoate | 2-Propenal, 3-(4-hexyl phenyl)-CAS313690-31-2 | $^1$H NMR (300 MHz, CDCl$_3$) δ 7.40 (d, J = 7.91 Hz, 2H), 7.07-7.18 (m, 3H), 6.80 (d, J = 15.53 Hz, 1H), 6.75 (dd, J = 1.17, 11.14 Hz, 1H), 4.33 (q, J = 7.23 Hz, 2H), 2.60 (t, J = 7.60 Hz, 2H), 1.57-1.65 (m, 2H), 1.37 (t, J = 7.18 Hz, 3H), 1.24-1.38 (m, 6H), 0.88 (t, J = 7.03 Hz, 3H) |
| 17 | ethyl (2Z,4E)-2-azido-5-(4-(3-phenylpropyl)phenyl)penta-2,4-dienoate | Intermediate 14 | $^1$H NMR (300 MHz, CDCl$_3$) δ 7.40 (d, J = 8.21 Hz, 2H), 7.25-7.32 (m, 2H), 7.08-7.22 (m, 6H), 6.73-6.82 (m, 2H), 4.33 (q, J = 7.13 Hz, 2H), 2.65 (t, J = 7.62 Hz, 4H), 1.90-2.01 (m, 2H), 1.37 (t, J = 7.18 Hz, 3H) |

TABLE 2-continued

| Interm. number | IUPAC name | Starting Materials | $^1$H NMR δ (ppm) for Intermediate |
|---|---|---|---|
| 18 | ethyl (2Z,4E)-2-azido-5-(4-pentyloxyphenyl)penta-2,4-dienoate | 2-Propenal, 3-[4-(pentyloxy)phenyl]-CAS 66049-89-6 | $^1$H NMR (300 MHz, CDCl$_3$) δ 7.39-7.44 (m, 2H), 7.02 (dd, J = 11.70, 14.94 Hz, 1H), 6.84-6.89 (m, 2H), 6.73-6.79 (m, 2H), 4.32 (q, J = 7.13 Hz, 2H), 3.97 (t, J = 6.59 Hz, 2H), 1.74-1.84 (m, 2H), 1.36-1.48 (m, 4H), 1.38 (t, J = 7.20 Hz, 3H), 0.93 (t, J = 7.00 Hz, 3H) |

Example 11

Intermediate 19

Ethyl(2Z,4E)-5-(4-hexyl-3-propylphenyl)-2-[(triphenylphosphoranylidene)amino]penta-2,4-dienoate To a solution of Intermediate 15 (1.65 g, 4.47 mmol) in diethyl ether (22 mL) at 0° C. was added a solution of triphenylphosphine (1.17 g) in diethyl ether (11 mL). After stirring for 16 h at RT, the reaction mixture was concentrated under reduced pressure. Purification by MPLC (20% ethyl acetate in hexanes) gave 2.2 g ethyl (2Z,4E)-5-(4-hexyl-3-propylphenyl)-2-[(triphenylphosphoranylidene)amino]penta-2,4-dienoate as a yellow foam.

$^1$H NMR (300 MHz, CDCl$_3$) δ 7.64-7.80 (m, 7H), 7.39-7.51 (m, 9H), 7.23 (s, 1H), 7.13 (d, J=7.91 Hz, 1H), 7.05 (d, J=8.20 Hz, 1H), 6.73 (dd, J=3.81, 11.14 Hz, 1H), 6.60 (d, J=15.82 Hz, 1H), 3.89 (q, J=7.13 Hz, 2H), 2.57 (t, J=7.91 Hz, 4H), 1.51-1.70 (m, 4H), 1.26-1.43 (m, 6H), 0.96-1.06 (m, 6H), 0.85-0.92 (m, 3H).

Intermediates 20-22 were prepared from the corresponding starting materials, in a similar manner to the method described in Example 11 for Intermediate 19. The starting materials and the results are described below in Table 3.

TABLE 3

| Interm. number | IUPAC name | Starting material | $^1$H NMR δ (ppm) for Intermediate |
|---|---|---|---|
| 20 | ethyl (2Z,4E)-5-[4-(3-phenylpropyl)phenyl]-2-[(triphenylphosphoranylidene)amino]penta-2,4-dienoate | Intermediate 17 | $^1$H NMR (300 MHz, CDCl$_3$) δ 7.40 (d, J = 7.91 Hz, 2H), 7.07-7.18 (m, 3H), 6.80 (d, J = 15.53 Hz, 1H), 6.75 (dd, J = 1.17, 11.14 Hz, 1H), 4.33 (q, J = 7.23 Hz, 2H), 2.60 (t, J = 7.60 Hz, 2H), 1.57-1.65 (m, 2H), 1.37 (t, J = 7.18 Hz, 3H), 1.24-1.38 (m, 6H), 0.88 (t, J = 7.03 Hz, 3H) |
| 21 | ethyl (2Z,4E)-5-(4-hexylphenyl)-2-[(triphenylphosphoranylidene)amino]penta-2,4-dienoate | Intermediate 16 | $^1$H NMR (300 MHz, CDCl$_3$) δ 7.71-7.80 (m, 6H), 7.66 (dd, J = 11.14, 15.82 Hz, 1H), 7.39-7.53 (m, 9H), 7.29 (d, J = 8.21 Hz, 2H), 7.10 (s, 2H), 6.72 (dd, J = 3.66, 10.70 Hz, 1H), 6.62 (d, J = 15.82 Hz, 1H), 3.90 (q, J = 7.13 Hz, 2H), 2.57 (t, J = 7.60 Hz, 2H), 1.54-1.65 (m, 2H), 1.25-1.37 (m, 6H), 1.04 (t, J = 7.18 Hz, 3H), 0.88 (t, J = 7.00 Hz, 3H) |
| 22 | ethyl(2Z,4E)-5-(4-pentyl oxyphenyl)-2-[(triphenylphosphoranylidene)amino]penta-2,4-dienoate | Intermediate 18 | $^1$H NMR (300 MHz, CDCl$_3$) δ 7.71-7.80 (m, 6H), 7.39-7.60 (m, 10H), 7.29 (d, J = 8.50 Hz, 2H), 6.81 (d, J = 8.79 Hz, 2H), 6.72 (dd, J = 3.37, 10.99 Hz, 1H), 6.59 (d, J = 15.82 Hz, 1H), 3.96 (d, J = 13.19 Hz, 2H), 3.90 (q, J = 7.00 Hz, 2H), 1.73-1.83 (m, 2H), 1.32-1.50 (m, 4H), 1.04 (t, J = 7.18 Hz, 3H), 0.94 (t, J = 6.74 Hz, 3H) |

Example 12

Intermediate 23

Ethyl 5-(4-hexylphenyl)-6-(3-thienyl)pyridine-2-carboxylate

To a solution of Intermediate 21 (766 mg, 1.36 mmol) in acetonitrile (20 mL) was added thiophene-3-carbaldehyde (0.12 mL, 1.36 mmol). After stirring at 65° C. for 16 h, the reaction mixture was concentrated under reduced pressure and purified by MPLC (10% ethyl acetate in hexanes) to afford 350 mg of ethyl 5-(4-hexylphenyl)-6-(3-thienyl)pyridine-2-carboxylate as a yellow oil.

$^1$H NMR (300 MHz, CDCl$_3$) δ 7.97 (d, J=7.91 Hz, 1H), 7.67 (d, J=7.91 Hz, 1H), 7.06-7.14 (m, 5H), 7.00-7.05 (m, 2H), 4.41 (q, J=7.03 Hz, 2H), 2.56 (t, J=7.91 Hz, 2H), 1.45-1.66 (m, 2H), 1.38 (t, J=7.03 Hz, 3H), 1.17-1.32 (m, 6H), 0.77-0.84 (m, 3H).

Intermediates 24-39 were prepared from the corresponding starting materials, in a similar manner to the method described in Example 12 for Intermediate 23. The starting materials and the results are described below in Table 4.

TABLE 4

| Interm. number | IUPAC name | Starting material | $^1$H NMR δ (ppm) for Intermediate |
|---|---|---|---|
| 24 | Ethyl-5-(4-hexylphenyl)-6-phenylpyridine-2-carboxylate | Intermediate 21 Benzaldehyde CAS 100-52-7 | $^1$H NMR (300 MHz, CDCl$_3$) δ 8.10 (d, J = 8.20 Hz, 1H), 7.83 (d, J = 7.91 Hz, 1H), 7.38-7.42 (m, 2H), 7.20-7.26 (m, 2H), 7.08 (s, 5H), 4.49 (q, J = 7.23 Hz, 2H), 2.56-2.61 (m, 2H), 1.54-1.64 (m, 2H), 1.45 (t, J = 7.18 Hz, 3H), 1.25-1.35 (m, 6H), 0.88 (t, J = 6.70 Hz, 3H) |
| 25 | Ethyl-5-(4-hexyl-3-propylphenyl)-6-phenylpyridine-2-carboxylate | Intermediate 19 Benzaldehyde CAS 100-52-7 | $^1$H NMR (300 MHz, CDCl$_3$) δ 8.09 (d, J = 7.91 Hz, 1H), 7.83 (d, J = 7.91 Hz, 1H), 7.38-7.42 (m, 2H), 7.19-7.24 (m, 3H), 7.07 (d, J = 7.91 Hz, 1H), 6.97 (dd, J = 2.05, 7.62 Hz, 1H), 6.89 (s, 1H), 4.48 (q, J = 7.23 Hz, 2H), 2.57 (t, J = 7.60 Hz, 2H), 2.45 (t, J = 7.80 Hz, 2H), 1.50-1.65 (m, 2H), 1.40-1.48 (m, J = 7.18, 7.18 Hz, 3H), 1.24-1.48 (m, 8H), 0.89 (t, J = 6.45 Hz, 3H), 0.82 (t, J = 7.33 Hz, 3H) |
| 26 | Ethyl-6-(3-chlorophenyl)-5-(4-hexyl-3-propylphenyl)pyridine-2-carboxylate | Intermediate 19 3-chloro-benzaldehyde CAS 587-04-2 | $^1$H NMR (300 MHz, CDCl$_3$) δ 8.12 (d, J = 8.20 Hz, 1H), 7.85 (d, J = 7.91 Hz, 1H), 7.45-7.47 (m, 1H), 7.19-7.24 (m, 2H), 7.13 (d, J = 7.33 Hz, 1H), 7.10 (d, J = 7.91 Hz, 1H), 6.96 (dd, J = 1.76, 7.91 Hz, 1H), 6.89 (d, J = 1.47 Hz, 1H), 4.50 (q, J = 7.13 Hz, 2H), 2.59 (t, J = 7.60 Hz, 2H), 2.49 (t, J = 7.60 Hz, 2H), 1.51-1.61 (m, 2H), 1.45 (d, J = 14.07 Hz, 3H), 1.26-1.48 (m, 8H), 0.86-0.92 (m, J = 6.70, 6.70 Hz, 3H), 0.85 (t, J = 7.00 Hz, 3H) |
| 27 | Ethyl-6-phenyl-5-[4-(3-phenylpropyl)phenyl]pyridine-2-carboxylate | Intermediate 20 Benzaldehyde CAS 100-52-7 | $^1$H NMR (300 MHz, CDCl$_3$) δ 8.11 (d, J = 7.91 Hz, 1H), 7.83 (d, J = 7.91 Hz, 1H), 7.38-7.42 (m, 2H), 7.15-7.31 (m, 8H), 7.09 (s, 4H), 4.49 (q, J = 7.23 Hz, 2H), 2.60-2.66 (m, 4H), 1.89-2.00 (m, 2H), 1.45 (t, J = 7.03 Hz, 3H) |
| 28 | Ethyl-6-(3-chlorophenyl)-5-[4-(3-phenylpropyl)phenyl]pyridine-2-carboxylate | Intermediate 20 3-chloro-benzaldehyde CAS 587-04-2 | $^1$H NMR (300 MHz, CDCl$_3$) δ 8.13 (d, J = 7.91 Hz, 1H), 7.85 (d, J = 7.91 Hz, 1H), 7.49 (t, J = 1.76 Hz, 1H), 7.07-7.31 (m, 12H), 4.50 (q, J = 7.23 Hz, 2H), 2.61-2.68 (m, 4H), 1.90-2.01 (m, 2H), 1.46 (t, J = 7.03 Hz, 3H) |
| 29 | Ethyl-5-(4-hexylphenyl)-6-(3-hydroxyphenyl)pyridine-2-carboxylate | Intermediate 21 3-hydroxy-benzaldehyde CAS 100-83-4 | $^1$H NMR (300 MHz, CDCl$_3$) δ 8.14 (d, J = 7.91 Hz, 1H), 7.87 (d, J = 7.91 Hz, 1H), 7.20 (s, 1H), 7.06-7.13 (m, 4H), 6.92 (t, J = 7.62 Hz, 1H), 6.74 (br. s., 1H), 6.58-6.64 (m, 2H), |

TABLE 4-continued

| Interm. number | IUPAC name | Starting material | $^1$H NMR δ (ppm) for Intermediate |
|---|---|---|---|
| | | | 4.47 (q, J = 7.23 Hz, 2H), 2.58 (t, J = 7.91 Hz, 2H), 1.54-1.63 (m, 2H), 1.40 (t, J = 7.03 Hz, 3H), 1.24-1.34 (m, 6H), 0.88 (t, J = 6.74 Hz, 3H) |
| 30 | Ethyl-5-[4-(pentyloxy)phenyl]-6-phenylpyridine-2-carboxylate | Intermediate 22 Benzaldehyde CAS 100-52-7 | $^1$H NMR (300 MHz, CDCl$_3$) δ 8.10 (d, J = 7.91 Hz, 1H), 7.81 (d, J = 7.91 Hz, 1H), 7.40-7.44 (m, 2H), 7.22-7.27 (m, 3H), 7.06-7.11 (m, 2H), 6.78-6.83 (m, 2H), 4.49 (q, J = 7.00 Hz, 2H), 3.93 (t, J = 6.59 Hz, 2H), 1.73-1.83 (m, 2H), 1.45 (t, J = 7.03 Hz, 3H), 1.31-1.49 (m, 4H), 0.93 (t, J = 7.33 Hz, 3H) |
| 31 | Ethyl-6-(4-fluorophenyl)-5-[4-(pentyloxy)phenyl]pyridine-2-carboxylate | Intermediate 22 4-fluoro-benzaldehyde CAS 459-57-4 | $^1$H NMR (300 MHz, CDCl$_3$) δ 8.09 (d, J = 7.91 Hz, 1H), 7.81 (d, J = 7.91 Hz, 1H), 7.40 (dd, J = 5.42, 8.94 Hz, 2H), 7.05-7.11 (m, 2H), 6.90-6.98 (m, 2H), 6.80-6.85 (m, 2H), 4.49 (q, J = 7.03 Hz, 2H), 3.95 (t, J = 6.59 Hz, 2H), 1.73-1.84 (m, 2H), 1.45 (t, J = 7.18 Hz, 3H), 1.34-1.47 (m, 4H), 0.94 (t, J = 7.30 Hz, 3H) |
| 32 | Ethyl-6-(3-fluorophenyl)-5-[4-(pentyloxy)phenyl]pyridine-2-carboxylate | Intermediate 22 3-fluoro-benzaldehyde CAS 456-48-4 | $^1$H NMR (300 MHz, CDCl$_3$) δ 8.12 (d, J = 7.91 Hz, 1H), 7.83 (d, J = 8.20 Hz, 1H), 7.11-7.24 (m, 3H), 7.09 (d, J = 8.79 Hz, 1H), 7.09 (q, J = 4.98 Hz, 1H), 6.92-7.00 (m, 1H), 6.80-6.85 (m, 2H), 4.49 (q, J = 7.13 Hz, 2H), 3.95 (t, J = 6.59 Hz, 2H), 1.74-1.84 (m, 2H), 1.46 (t, J = 7.00 Hz, 3H), 1.32-1.50 (m, 4H), 0.93 (t, J = 6.70 Hz, 3H) |
| 33 | Ethyl-5-(4-hexylphenyl)-6-(2-thienyl)pyridine-2-carboxylate | Intermediate 21 2-Thiophene carboxaldehyde CAS 98-03-3 | $^1$H NMR (300 MHz, CDCl$_3$) δ 7.56 (d, J = 7.91 Hz, 1H), 7.27 (d, J = 5.86 Hz, 1H), 7.23 (s, 4H), 7.11 (d, J = 7.62 Hz, 1H), 6.76-6.86 (m, 1H), 6.62 (d, J = 3.81 Hz, 1H), 4.81 (s, 2H), 3.92-4.07 (m, 1H), 2.68 (t, J = 7.77 Hz, 2H), 1.62-1.72 (m, 2H), 1.27-1.42 (m, 6H), 0.90 (t, J = 6.74 Hz, 3H) |
| 34 | Ethyl-6-(5-fluoro-2-thienyl)-5-(4-hexylphenyl)pyridine-2-carboxylate | Intermediate 21 5-fluoro-2-Thiophenecarboxaldehyde CAS 29669-49-6 | $^1$H NMR (300 MHz, CDCl$_3$) δ 7.02-7.09 (m, 5H), 6.98 (t, J = 3.96 Hz, 1H), 6.60 (dd, J = 2.78, 6.59 Hz, 1H), 6.36 (dd, J = 1.47, 4.10 Hz, 1H), 4.31 (q, J = 7.33 Hz, 2H), 2.53 (dd, J = 7.62, 8.20 Hz, 2H), 1.50-1.59 (m, 2H), 1.36 (t, J = 7.18 Hz, 3H), 1.23-1.33 (m, 6H), 0.83-0.91 (m, 3H) |
| 35 | Ethyl-5-(4-hexyl-3-propylphenyl)-6-(2-thienyl)pyridine-2-carboxylate | Intermediate 19 2-Thiophenecarboxaldehyde CAS 98-03-3 | $^1$H NMR (300 MHz, CDCl$_3$) δ 7.98 (d, J = 7.62 Hz, 1H), 7.69 (d, J = 7.91 Hz, 1H), 7.28 (d, J = 4.98 Hz, 1H), 7.21 (d, J = 7.33 Hz, 1H), 7.06-7.12 (m, 2H), 6.81 (dd, J = 3.81, 4.98 Hz, 1H), 6.75 (d, J = 3.52 Hz, 1H), 4.49 (q, J = 7.23 Hz, 2H), 2.68 (t, J = 7.62 Hz, 1H), 2.60 (dd, J = 7.33, 7.91 Hz, 2H), 1.48 (t, J = 7.03 Hz, 3H), 1.32-1.69 (m, 10H), 0.89-0.99 (m, 6H)\ |
| 36 | Ethyl-5-[4-(3-phenylpropyl)phenyl]-6-(2-thienyl)pyridine-2-carboxylate | Intermediate 20 2-Thiophene carboxaldehyde CAS 98-03-3 | $^1$H NMR (300 MHz, CDCl$_3$) δ 7.99 (d, J = 7.91 Hz, 1H), 7.67 (s, 1H), 7.17-7.33 (m, 10H), 6.81 (t, J = 4.40 Hz, 1H), 6.72 (dd, J = 1.03, 3.66 Hz, 1H), |

TABLE 4-continued

| Interm. number | IUPAC name | Starting material | $^1$H NMR δ (ppm) for Intermediate |
|---|---|---|---|
| | | | 4.49 (q, J = 7.23 Hz, 2H), 2.71 (dt, J = 7.76, 11.13 Hz, 4H), 2.01 (quin, J = 7.69 Hz, 2H), 1.47 (t, J = 7.03 Hz, 3H) |
| 37 | Ethyl-5-(4-hexylphenyl)-6-(1,3-oxazol-4-yl)pyridine-2-carboxylate | Intermediate 21 4-Oxazolecarboxaldehyde CAS 118994-84-6 | $^1$H NMR (300 MHz, CDCl$_3$) δ 8.11 (d, J = 7.91 Hz, 1H), 7.83 (s, 1H), 7.78 (d, J = 7.91 Hz, 1H), 7.31 (s, 1H), 7.17-7.27 (m, 4H), 4.51 (q, J = 7.23 Hz, 2H), 2.66 (t, J = 7.77 Hz, 2H), 1.60-1.70 (m, 2H), 1.47 (t, J = 7.18 Hz, 3H), 1.33 (br. s., 6H), 0.90 (t, J = 6.74 Hz, 3H) |
| 38 | Ethyl-5-(4-hexylphenyl)-6-(1,3-thiazol-2-yl)pyridine-2-carboxylate | Intermediate 21 2-Thiazole carboxaldehyde CAS 10200-59-6 | $^1$H NMR (300 MHz, CDCl$_3$) δ 8.15 (d, J = 7.91 Hz, 1H), 7.86 (d, J = 7.91 Hz, 1H), 7.69 (d, J = 3.22 Hz, 1H), 7.37 (d, J = 3.22 Hz, 1H), 7.15-7.25 (m, 4H), 4.51 (q, J = 7.23 Hz, 2H), 2.65 (t, J = 7.77 Hz, 2H), 1.59-1.69 (m, 2H), 1.47 (t, J = 7.03 Hz, 3H), 1.22-1.39 (m, 6H), 0.89 (t, J = 6.30 Hz, 3H) |
| 39 | Ethyl-6-(2-furyl)-5-(4-hexylphenyl)pyridine-2-carboxylate | Intermediate 21 2-Furancarboxaldehyde CAS 98-01-1 | $^1$H NMR (300 MHz, CDCl$_3$) δ 8.03 (d, J = 7.91 Hz, 1H), 7.72 (d, J = 7.91 Hz, 1H), 7.42 (s, 1H), 7.18-7.26 (m, 4H), 6.28 (dd, J = 1.76, 3.22 Hz, 1H), 6.09 (d, J = 3.52 Hz, 1H), 4.51 (q, J = 7.03 Hz, 2H), 2.68 (t, J = 7.77 Hz, 2H), 1.58-1.72 (m, 2H), 1.48 (t, J = 7.18 Hz, 3H), 1.29-1.39 (m, 6H), 0.87-0.94 (m, 3H) |

Example 13

Intermediate 40

[5-(4-hexylphenyl)-6-(3-thienyl)pyridin-2-yl]methanol

To a solution of Intermediate 23 (350 mg, 0.89 mmol) in dichloromethane (10 mL) at −78° C. was added DIBAL-H (1.0 M in dichloromethane, 4.5 mL). The reaction was warmed to RT over for 3 h with stirring and was quenched at −10° C. with ethyl acetate methanol, and 10% solution of HCl. The mixture was diluted with water. The aqueous layer was washed with ethyl acetate. The combined organic layers were washed with brine, dried over Na$_2$SO$_4$, and concentrated under reduced pressure. The residue was purified by MPLC (40% ethyl acetate in hexanes) to give 227 mg of the desired alcohol as colorless oil. $^1$H NMR (300 MHz, CDCl$_3$) δ 7.64 (d, J=7.91 Hz, 1H), 7.25 (dd, J=1.32, 2.78 Hz, 1H), 7.11-7.19 (m, 5H), 7.13 (d, J=2.93 Hz, 1H), 7.09 (dd, J=1.17, 4.98 Hz, 1H), 4.82 (s, 2H), 2.64 (t, J=7.62 Hz, 2H), 1.58-1.69 (m, 2H), 1.32 (br. s., 6H), 0.90 (t, J=6.45 Hz, 3H)

Intermediates 41-61 were prepared from the corresponding starting materials, in a similar manner to the method described in Example 13 for Intermediate 40. The starting materials and the results are described below in Table 5.

TABLE 5

| Interm. number | IUPAC name | starting material | $^1$H NMR δ (ppm) for Intermediate |
|---|---|---|---|
| 41 | (4-octyl-1,1':2',1''-terphenyl-4'-yl)methanol | Intermediate 4 | $^1$H NMR (300 MHz, CDCl$_3$) δ 7.39-7.46 (m, 3H), 7.14-7.24 (m, 5H), 7.04 (s, 4H), 4.77 (s, 2H), 2.57 (t, J = 7.62 Hz, 2H), 1.55-1.64 (m, 2H), 1.25-1.36 (m, 10H), 0.88-0.95 (m, 3H) |
| 42 | [6-(6-hexylpyridin-3-yl)biphenyl-3-yl]methanol | Intermediate 5 | $^1$H NMR (300 MHz, CDCl$_3$) δ 8.03-8.06 (m, J = 0.59, 2.30 Hz, 1H), 7.42 (s, 2H), 7.35 (d, J = 7.91 Hz, 1H), 7.17-7.24 (m, 4H), 7.04-7.08 (m, 2H), 6.93 (d, J = 7.91 Hz, 1H), 4.77 (s, 2H), 2.73 (t, J = 7.30 Hz, 2H), 1.62-1.73 (m, 2H), 1.25-1.34 (m, 6H), 0.87 (t, J = 6.74 Hz, 3H) |

TABLE 5-continued

| Interm. number | IUPAC name | starting material | ¹H NMR δ (ppm) for Intermediate |
|---|---|---|---|
| 43 | [4-(3,3,4,4,5,5,6,6,6-nonafluorohexyl)-1,1':2',1''-terphenyl-4'-yl]methanol | Intermediate 7 | ¹H NMR (300 MHz, CDCl$_3$) δ 7.42 (s, 3H), 7.19-7.24 (m, 3H), 7.10-7.16 (m, 2H), 7.04-7.09 (m, 4H), 4.78 (s, 2H), 2.84-2.90 (m, 2H), 2.25-2.44 (m, 2H), 1.70 (br. s., 1H) |
| 44 | [5-(4-hexylphenyl)-6-phenylpyridin-2-yl]methanol | Intermediate 24 | ¹H NMR (300 MHz, CDCl$_3$) δ 7.71 (d, J = 7.62 Hz, 1H), 7.35-7.39 (m, 2H), 7.21-7.26 (m, 3H), 7.07 (s, 5H), 4.83 (s, 2H), 2.55-2.61 (m, 2H), 1.53-1.64 (m, 2H), 1.31 (s, 6H), 0.88 (t, J = 6.15 Hz, 3H) |
| 45 | 4-(3-phenylpropyl)-1,1':2',1''-terphenyl-4'-methanol | Intermediate 8 | ¹H NMR (300 MHz, CDCl$_3$) δ 7.37-7.44 (m, 3H), 7.24-7.30 (m, 2H), 7.11-7.20 (m, 7H), 6.99-7.05 (m, 4H), 4.75 (s, 2H), 2.60 (td, J = 3.81, 7.62 Hz, 4H), 1.87-1.98 (m, 2H), 1.76 (s, OH) |
| 46 | [5-(4-hexyl-3-propylphenyl)-6-phenylpyridin-2-yl]methanol | Intermediate 25 | ¹H NMR (300 MHz, CDCl$_3$) δ 7.72 (d, J = 7.91 Hz, 1H), 7.34-7.38 (m, 2H), 7.20-7.25 (m, 4H), 7.06 (d, J = 7.62 Hz, 1H), 6.95 (dd, J = 2.05, 7.33 Hz, 1H), 6.87 (d, J = 1.76 Hz, 1H), 4.82 (s, 2H), 2.57 (t, J = 7.90 Hz, 2H), 2.45 (t, J = 7.60 Hz, 2H), 1.50-1.61 (m, 2H), 1.26-1.44 (m, 8H), 0.89 (t, J = 6.40 Hz, 3H), 0.82 (t, J = 7.33 Hz, 3H) |
| 47 | [6-(6-octylpyridin-3-yl)biphenyl-3-yl]methanol | Intermediate 6 | ¹H NMR (300 MHz, CDCl$_3$) δ 8.14 (dd, J = 0.59, 2.34 Hz, 1H), 7.36-7.45 (m, 3H), 7.18-7.26 (m, 4H), 7.06-7.11 (m, 2H), 6.94 (d, J = 7.91 Hz, 1H), 4.78 (s, 2H), 2.84 (br. s., 1H), 2.73 (t, J = 7.60 Hz, 2H), 1.63-1.73 (m, 2H), 1.23-1.34 (m, 10H), 0.87 (t, J = 7.00 Hz, 3H) |
| 48 | [6-(3-chlorophenyl)-5-(4-hexyl-3-propylphenyl)pyridin-2-yl]methanol | Intermediate 26 | ¹H NMR (300 MHz, CDCl$_3$) δ 7.73 (d, J = 7.91 Hz, 1H), 7.41 (t, J = 1.76 Hz, 1H), 7.27 (d, J = 7.91 Hz, 1H), 7.20 (tt, J = 2.10, 7.60 Hz, 2H), 7.13 (d, J = 7.62 Hz, 2H), 7.08 (d, J = 7.91 Hz, 1H), 6.94 (dd, J = 1.90, 7.77 Hz, 1H), 6.87 (d, J = 1.76 Hz, 1H), 4.83 (s, 2H), 2.59 (t, J = 7.60 Hz, 2H), 2.48 (t, J = 7.60 Hz, 2H), 1.50-1.61 (m, 2H), 1.25-1.48 (m, 8H), 0.86-0.93 (m, J = 6.40, 6.40 Hz, 3H), 0.84 (t, J = 7.30 Hz, 3H) |
| 49 | {6-(3-chlorophenyl)-5-[4-(3-phenylpropyl)phenyl]pyridin-2-yl}methanol | Intermediate 28 | ¹H NMR (300 MHz, CDCl$_3$) δ 7.74 (d, J = 7.91 Hz, 1H), 7.45 (s, 1H), 7.06-7.31 (m, 13H), 4.85 (s, 2H), 2.61-2.68 (m, 4H), 1.90-2.01 (m, 2H) |
| 50 | 3-[3-(4-hexylphenyl)-6-(hydroxymethyl)pyridin-2-yl]phenol | Intermediate 29 | ¹H NMR (300 MHz, CDCl$_3$) δ 7.72 (d, J = 7.91 Hz, 1H), 7.27 (d, J = 7.91 Hz, 1H), 6.97-7.09 (m, 6H), 6.74 (d, J = 7.62 Hz, 2H), 4.83 (s, 2H), 2.58 (t, J = 7.77 Hz, 2H), 1.54-1.64 (m, 2H), 1.23-1.34 (m, 6H), 0.88 (t, J = 6.59 Hz, 3H) |

TABLE 5-continued

| Interm. number | IUPAC name | starting material | ¹H NMR δ (ppm) for Intermediate |
|---|---|---|---|
| 51 | 6-phenyl-5-[4-(3-phenylpropyl)phenyl]pyridine-2-methanol | Intermediate 27 | ¹H NMR (300 MHz, CDCl$_3$) 7.72 (d, J = 7.62 Hz, 1H), 7.36-7.39 (m, 2H), 7.15-7.31 (m, 9H), 7.08 (s, 4H), 4.84 (s, 2H), 2.63 (t, J = 7.60 Hz, 4H), 1.94 (t, J = 7.62 Hz, 2H) |
| 52 | {5-[4-(pentyloxy)phenyl]-6-phenylpyridin-2-yl}methanol | Intermediate 30 | ¹H NMR (300 MHz, CDCl$_3$) δ 7.69 (d, J = 7.91 Hz, 1H), 7.35-7.41 (m, 2H), 7.21-7.27 (m, 4H), 7.03-7.09 (m, 2H), 6.76-6.82 (m, 2H), 4.82 (s, 2H), 3.92 (t, J = 6.59 Hz, 2H), 1.72-1.82 (m, 2H), 1.31-1.49 (m, 4H), 0.93 (t, J = 7.00 Hz, 3H) |
| 53 | {6-(4-fluorophenyl)-5-[4-(pentyloxy)phenyl]pyridin-2-yl}methanol | Intermediate 31 | ¹H NMR (300 MHz, CDCl$_3$) δ 7.69 (d, J = 7.91 Hz, 1H), 7.33-7.40 (m, 2H), 7.24 (d, J = 7.91 Hz, 1H), 7.03-7.09 (m, 2H), 6.90-6.98 (m, 2H), 6.78-6.84 (m, 2H), 4.82 (s, 2H), 3.94 (t, J = 6.59 Hz, 2H), 1.74-1.84 (m, 2H), 1.35-1.50 (m, 4H), 0.94 (t, J = 7.00 Hz, 3H) |
| 54 | {6-(3-fluorophenyl)-5-[4-(pentyloxy)phenyl]pyridin-2-yl}methanol | Intermediate 32 | ¹H NMR (300 MHz, CDCl$_3$) δ 7.71 (d, J = 7.91 Hz, 1H), 7.27 (d, J = 8.20 Hz, 1H), 7.09-7.24 (m, 3H), 7.07 (d, J = 8.79 Hz, 1H), 7.07 (q, J = 4.98 Hz, 1H), 6.96 (d, J = 1.17 Hz, 1H), 6.81 (d, J = 8.79 Hz, 1H), 6.81 (q, J = 5.00 Hz, 1H), 4.84 (s, 2H), 3.94 (t, J = 6.59 Hz, 2H), 3.86 (br. s., 1H), 1.74-1.84 (m, 2H), 1.32-1.50 (m, 4H), 0.93 (t, J = 7.00 Hz, 3H) |
| 55 | [5-(4-hexylphenyl)-6-(2-thienyl)pyridin-2-yl]methanol | Intermediate 33 | ¹H NMR (300 MHz, CDCl$_3$) δ 7.56 (d, J = 7.91 Hz, 1H), 7.27 (d, J = 5.86 Hz, 1H), 7.23 (s, 4H), 7.11 (d, J = 7.62 Hz, 1H), 6.76-6.86 (m, 1H), 6.62 (d, J = 3.81 Hz, 1H), 4.81 (s, 2H), 3.92-4.07 (m, 1H), 2.68 (t, J = 7.77 Hz, 2H), 1.62-1.72 (m, 2H), 1.27-1.42 (m, 6H), 0.90 (t, J = 6.74 Hz, 3H) |
| 56 | [6-(5-fluoro-2-thienyl)-5-(4-hexylphenyl)pyridin-2-yl]methanol | Intermediate 34 | ¹H NMR (300 MHz, CDCl$_3$) δ 7.51 (d, J = 7.91 Hz, 1H), 7.21-7.27 (m, 4H), 7.09 (d, J = 7.91 Hz, 1H), 6.16 (d, J = 2.64 Hz, 2H), 4.78 (s, 2H), 3.74 (br. s, 1H), 2.68 (t, J = 7.62 Hz, 2H), 1.62-1.72 (m, 2H), 1.27-1.39 (m, 6H), 0.90 (t, J = 6.45 Hz, 3H) |
| 57 | [5-(4-hexyl-3-propylphenyl)-6-(2-thienyl)pyridin-2-yl]methanol | Intermediate 35 | ¹H NMR (600 MHz, CDCl$_3$) δ 7.60 (d, J = 7.92 Hz, 1H), 7.24-7.29 (m, 1H), 7.20 (d, J = 7.63 Hz, 1H), 7.14 (d, J = 7.92 Hz, 1H), 7.04-7.10 (m, 2H), 6.82 (dd, J = 3.82, 4.99 Hz, 1H), 6.77 (d, J = 3.23 Hz, 1H), 4.82 (s, 2H), 3.41 (d, J = 6.46 Hz, 1H), 2.67 (dd, J = 7.90 Hz, 2H), 2.59 (dd, J = 7.34, 7.92 Hz, 2H), 1.53-1.65 (m, 4H), 1.33-1.44 (m, 4H), 0.90-0.95 (m, 6H) |
| 58 | {5-[4-(3-phenylpropyl)phenyl]-6-(2-thienyl)pyridin-2-yl}methanol | Intermediate 36 | ¹H NMR (300 MHz, CDCl$_3$) δ 7.54 (d, J = 7.91 Hz, 1H), 7.16-7.33 (m, 11H), 7.10 (d, J = 7.91 Hz, 1H), 6.79 (t, J = 4.40 Hz, |

TABLE 5-continued

| Interm. number | IUPAC name | starting material | $^1$H NMR δ (ppm) for Intermediate |
|---|---|---|---|
| | | | 1H), 6.62 (d, J = 3.52 Hz, 1H), 4.79 (s, 2H), 4.04 (br. s, 1H), 2.66-2.75 (m, 4H), 1.95-2.08 (m, 2H) |
| 59 | [5-(4-hexylphenyl)-6-(1,3-oxazol-4-yl)pyridin-2-yl]methanol | Intermediate 37 | $^1$H NMR (600 MHz, CDCl$_3$) δ 7.85 (d, J = 0.88 Hz, 1H), 7.62 (dd, J = 2.93, 7.92 Hz, 1H), 7.34 (d, J = 7.92 Hz, 1H), 7.22 (s, 2H), 7.14-7.19 (m, 2H), 6.98-7.01 (m, 1H), 4.90 (s, 2H), 4.52 (br. s, 1H), 2.66 (t, J = 7.78 Hz, 2H), 1.63-1.69 (m, 2H), 1.30-1.39 (m, 6H), 0.88-0.92 (m, 3H) |
| 60 | [5-(4-hexylphenyl)-6-(1,3-thiazol-2-yl)pyridin-2-yl]methanol | Intermediate 38 | $^1$H NMR (300 MHz, CDCl$_3$) δ 7.64-7.68 (m, 2H), 7.33 (d, J = 7.91 Hz, 1H), 7.27 (dd, J = 1.90, 3.08 Hz, 1H), 7.16 (s, 4H), 4.83 (s, 2H), 2.59-2.65 (m, 2H), 1.57-1.67 (m, 2H), 1.19-1.37 (m, 6H), 0.87 (t, J = 6.45 Hz, 3H) |
| 61 | [6-(2-furyl)-5-(4-hexylphenyl)pyridin-2-yl]methanol | Intermediate 39 | $^1$H NMR (300 MHz, CDCl$_3$) δ 7.59 (d, J = 7.91 Hz, 1H), 7.38 (s, 1H), 7.16-7.26 (m, 5H), 6.30 (dd, J = 1.76, 3.22 Hz, 1H), 6.10 (d, J = 3.22 Hz, 1H), 4.85 (s, 2H), 3.86 (br. s, 1H), 2.67 (t, J = 7.62 Hz, 2H), 1.61-1.71 (m, 2H), 1.27-1.42 (m, 6H), 0.90 (t, J = 7.03 Hz, 3H) |

Example 14

Intermediate 62

4-hexyl-1,1':2',1''-terphenyl-4'-carbaldehyde

To a vigorously stirred solution of pyridinium chlorochromate (1.29 g, 5.97 mmol) and celite (2.6 g) in dichloromethane (30 mL) was added a solution of (4-hexyl-1,1':2', 1''-terphenyl-4'-yl)methanol (1.37 g, 3.98 mmol) in dichloromethane. After stirring at RT for 3 h, the reaction mixture was filtered through a plug of silica gel and eluted well with dichloromethane. Concentration yielded 1.21 g of the aldehyde as colorless oil.

$^1$H NMR (300 MHz, CDCl$_3$) δ 10.08 (s, 1H), 7.92 (s, 1H), 7.90 (dd, J=1.80, 7.33 Hz, 1H), 7.57-7.60 (m, 1H), 7.21-7.26 (m, 3H), 7.13-7.17 (m, 2H), 7.05 (s, 4H), 2.54-2.59 (m, 2H), 1.58 (s, 2H), 1.25-1.33 (m, 6H), 0.88 (t, J=6.74 Hz, 3H).

Example 15

Intermediate 63

5-(4-hexylphenyl)-6-(3-thienyl)pyridine-2-carbaldehyde

To a solution of Intermediate 40 (70 mg, 0.2 mmol), NMO (58 mg, 0.5 mmol), and 4 A molecular sieves (140 mg) in dichloromethane (5 mL) and acetonitrile (0.6 mL) was added tetrapropylammonium perruthenate (TPAP, 4 mg). After stirring at RT for 2 h, the reaction mixture was filtered through a short column of silica gel, eluted with ethyl acetate and concentrated under reduced pressure. Purification by MPLC (10% ethyl acetate in hexanes) gave rise to 45 mg 5-(4-hexylphenyl)-6-(3-thienyl)pyridine-2-carbaldehyde as a yellow oil.

$^1$H NMR (300 MHz, CDCl$_3$) δ 10.15 (s, 1H), 7.91 (d, J=8.20 Hz, 1H), 7.80 (d, J=7.91 Hz, 1H), 7.33 (dd, J=1.17, 2.93 Hz, 1H), 7.12-7.22 (m, 6H), 2.65 (t, J=7.77 Hz, 2H), 1.59-1.69 (m, 2H), 1.25-1.41 (m, 6H), 0.90 (t, J=6.45 Hz, 3H).

Intermediates 64-84 were prepared from the corresponding starting materials, in a similar manner to the method described in Example 14 for Intermediate 62 or Example 15 for Intermediate 63. The starting materials and the results are described below in Table 6.

TABLE 6

| Intermediate number | IUPAC name | starting material | $^1$H NMR δ (ppm) for Intermediate |
|---|---|---|---|
| 65 | 5-(4-hexylphenyl)-6-phenylpyridine-2-carbaldehyde | Intermediate 44 | $^1$H NMR (300 MHz, CDCl$_3$) δ 10.18 (d, J = 0.88 Hz, 1H), 7.98 (d, J = 8.20 Hz, 1H), |

TABLE 6-continued

| Intermediate number | IUPAC name | starting material | $^1$H NMR δ (ppm) for Intermediate |
|---|---|---|---|
| | | | 7.89 (dd, J = 0.88, 7.91 Hz, 1H), 7.40-7.43 (m, 2H), 7.25-7.31 (m, 3H), 7.10 (s, 4H), 2.59 (dd, J = 7.60 Hz, 2H), 1.55-1.65 (m, 2H), 1.25-1.34 (m, 6H), 0.88 (t, J = 6.70 Hz, 3H) |
| 66 | 6-(6-hexylpyridin-2-yl)biphenyl-3-carbaldehyde | Intermediate 42 | $^1$H NMR (300 MHz, CDCl$_3$) δ 10.11 (s, 1H), 8.39 (dd, J = 0.88, 2.34 Hz, 1H), 7.93-7.97 (m, 2H), 7.59 (d, J = 8.50 Hz, 1H), 7.25-7.31 (m, 4H), 7.12-7.16 (m, 2H), 7.00 (dd, J = 0.59, 8.20 Hz, 1H), 2.76 (t, J = 8.00 Hz, 2H), 1.60-1.75 (m, 2H), 1.26-1.35 (m, 6H), 0.88 (t, J = 6.74 Hz, 3H). |
| 67 | 4-(3-phenylpropyl)-1,1':2',1''-terphenyl-4'-carbaldehyde | Intermediate 45 | $^1$H NMR (300 MHz, CDCl$_3$) δ 10.08 (s, 1H), 7.88-7.92 (m, 2H), 7.58 (d, J = 8.50 Hz, 1H), 7.13-7.30 (m, 10H), 7.05 (s, 4H), 2.61 (t, J = 7.62 Hz, 4H), 1.88-1.99 (m, 2H). |
| 68 | 6-phenyl-5-[4-(3-phenylpropyl)phenyl]pyridine-2-carbaldehyde | Intermediate 51 | $^1$H NMR (300 MHz, CDCl$_3$) δ 10.18 (s, 1H), 7.97-8.00 (m, 1H), 7.89 (d, J = 7.91 Hz, 1H), 7.39-7.43 (m, 2H), 7.25-7.31 (m, 4H), 7.15-7.21 (m, 3H), 7.11 (s, 4H), 2.64 (td, J = 2.93, 7.90 Hz, 4H), 1.90-2.00 (m, 2H) |
| 69 | 5-(4-hexylphenyl)-6-(3-hydroxyphenyl)pyridine-2-carbaldehyde | Intermediate 50 | $^1$H NMR (300 MHz, CDCl$_3$) δ 10.18 (s, 1H), 7.99 (d, J = 8.20 Hz, 1H), 7.90 (d, J = 7.62 Hz, 1H), 7.01-7.13 (m, 6H), 6.82-6.85 (m, 1H), 6.76 (ddd, J = 1.20, 2.34, 8.20 Hz, 1H), 2.60 (t, J = 7.90 Hz, 2H), 1.59 (d, J = 7.33 Hz, 2H), 1.25-1.34 (m, 6H), 0.88 (t, J = 6.45 Hz, 3H) |
| 70 | 5-(4-hexyl-3-propylphenyl)-6-phenylpyridine-2-carbaldehyde | Intermediate 46 | $^1$H NMR (300 MHz, CDCl$_3$) δ 10.18 (d, J = 0.59 Hz, 2H), 7.97 (d, J = 7.91 Hz, 1H), 7.89 (d, J = 7.62 Hz, 1H), 7.39-7.43 (m, 2H), 7.25-7.30 (m, 3H), 7.07-7.11 (m, 1H), 6.99 (dd, J = 2.05, 7.91 Hz, 1H), 6.91 (d, J = 1.76 Hz, 1H), 2.58 (t, J = 7.90 Hz, 2H), 2.46 (t, J = 7.60 Hz, 2H), 1.50-1.62 (m, 2H), 1.26-1.45 (m, 8H), 0.90 (t, J = 6.70 Hz, 3H), 0.83 (t, J = 7.33 Hz, 3H) |
| 71 | 6-(3-chlorophenyl)-5-(4-hexyl-3-propylphenyl)pyridine-2-carbaldehyde | Intermediate 48 | $^1$H NMR (300 MHz, CDCl$_3$) δ 10.16 (s, 1H), 7.98 (d, J = 7.91 Hz, 1H), 7.90 (d, J = 8.21 Hz, 1H), 7.47 (t, J = 1.76 Hz, 1H), 7.24 (tt, J = 1.47, 7.60 Hz, 2H), 7.17 (d, J = 7.62 Hz, 1H), 7.11 (d, J = 7.91 Hz, 1H), 6.98 (dd, J = 1.47, 7.62 Hz, 1H), 6.91 (d, J = 1.76 Hz, 1H), 2.60 (t, J = 7.60 Hz, 2H), 2.49 (t, J = 7.33 Hz, 2H), 1.51-1.62 (m, 2H), 1.28-1.49 (m, 8H), 0.86-0.93 (m, J = 6.70, 6.70 Hz, 3H), 0.85 (t, J = 7.30 Hz, 3H) |
| 72 | 6-(3-chlorophenyl)-5-[4-(3-phenylpropyl)phenyl]pyridine-2-carbaldehyde | Intermediate 49 | $^1$H NMR (300 MHz, CDCl$_3$) δ 10.17 (s, 3H), 8.00 (d, J = 7.91 Hz, 1H), 7.90 (d, J = 7.91 Hz, 1H), 7.50 (s, 1H), 7.26-7.31 (m, 3H), |

TABLE 6-continued

| Intermediate number | IUPAC name | starting material | ¹H NMR δ (ppm) for Intermediate |
|---|---|---|---|
| | | | 7.09-7.22 (m, 9H), 2.65 (dt, J = 6.70, 7.33 Hz, 4H), 1.96 (quin, J = 7.62 Hz, 2H) |
| 73 | 4-(3,3,4,4,5,5,6,6,6-nonafluorohexyl)-1,1':2',1''-terphenyl-4'-carbaldehyde | Intermediate 43 | ¹H NMR (300 MHz, CDCl$_3$) δ 10.09 (s, 1H), 7.91-7.98 (m, 1H), 7.91 (dd, J = 1.50, 6.45 Hz, 1H), 7.57 (d, J = 8.50 Hz, 1H), 7.22-7.27 (m, 3H), 7.12-7.17 (m, 2H), 7.07-7.11 (m, 4H), 2.86-2.91 (m, 2H), 2.26-2.45 (m, 2H) |
| 74 | 5-[4-(pentyloxy)phenyl]-6-phenylpyridine-2-carbaldehyde | Intermediate 52 | ¹H NMR (300 MHz, CDCl$_3$) δ 10.17 (d, J = 0.59 Hz, 1H), 7.97 (d, J = 7.62 Hz, 1H), 7.87 (dd, J = 0.88, 7.91 Hz, 1H), 7.40-7.46 (m, 2H), 7.28-7.33 (m, 3H), 7.08-7.13 (m, 2H), 6.79-6.84 (m, 2H), 3.94 (t, J = 6.59 Hz, 2H), 1.73-1.83 (m, 2H), 1.33-1.49 (m, 4H), 0.93 (t, J = 7.30 Hz, 3H) |
| 75 | 6-(3-fluorophenyl)-5-[4-(pentyloxy)phenyl]pyridine-2-carbaldehyde | Intermediate 54 | ¹H NMR (300 MHz, CDCl$_3$) δ 10.17 (d, J = 0.60 Hz, 1H), 8.00 (d, J = 7.91 Hz, 1H), 7.90 (dd, J = 0.60, 7.90 Hz, 1H), 7.10-7.30 (m, 5H), 6.99-7.06 (m, 1H), 6.81-6.88 (m, 2H), 3.97 (t, J = 6.59 Hz, 2H), 1.81 (tdd, J = 6.74, 6.96, 7.07 Hz, 2H), 1.34-1.52 (m, 4H), 0.90-1.01 (m, 3H) |
| 76 | 6-(4-fluorophenyl)-5-[4-(pentyloxy)phenyl]pyridine-2-carbaldehyde | Intermediate 53 | ¹H NMR (300 MHz, CDCl$_3$) δ 10.14 (d, J = 0.59 Hz, 1H), 7.95 (d, J = 7.91 Hz, 1H), 7.85 (dd, J = 0.88, 7.62 Hz, 1H), 7.38-7.45 (m, 2H), 7.07-7.12 (m, 2H), 6.94-7.02 (m, 2H), 6.80-6.86 (m, 2H), 3.95 (t, J = 6.59 Hz, 2H), 1.73-1.84 (m, 2H), 1.34-1.50 (m, 4H), 0.93 (t, J = 7.00 Hz, 3H) |
| 77 | 4-octyl-1,1':2',1''-terphenyl-4'-carbaldehyde | Intermediate 41 | ¹H NMR (300 MHz, CDCl$_3$) δ 10.08 (s, 1H), 7.91-7.93 (m, 1H), 7.90 (dd, J = 1.47, 7.03 Hz, 1H), 7.59 (d, J = 8.50 Hz, 1H), 7.22-7.26 (m, 3H), 7.13-7.17 (m, 2H), 7.05 (s, 4H), 2.53-2.59 (m, 2H), 1.55 (s, 2H), 1.24-1.32 (m, 10H), 0.88 (t, J = 6.74 Hz, 3H) |
| 78 | 5-(4-hexylphenyl)-6-(2-thienyl)pyridine-2-carbaldehyde | Intermediate 55 | ¹H NMR (300 MHz, CDCl$_3$) δ 10.10 (s, 1H), 7.80 (d, J = 7.62 Hz, 1H), 7.68 (d, J = 7.62 Hz, 1H), 7.28 (d, J = 4.98 Hz, 1H), 7.21 (s, 4H), 6.80 (t, J = 4.40 Hz, 1H), 6.68 (d, J = 3.52 Hz, 1H), 2.65 (t, J = 7.62 Hz, 2H), 1.63 (s, 2H), 1.23-1.39 (m, 6H), 0.87 (t, J = 6.30 Hz, 3H) |
| 79 | 6-(5-fluoro-2-thienyl)-5-(4-hexylphenyl)pyridine-2-carbaldehyde | Intermediate 56 | ¹H NMR (600 MHz, CDCl$_3$) δ 10.09 (d, J = 0.59 Hz, 1H), 7.81 (d, J = 7.92 Hz, 1H), 7.67 (dd, J = 0.88, 7.92 Hz, 1H), 7.24-7.29 (m, 4H), 6.26 (dd, J = 3.67, 4.26 Hz, 1H), 6.19 (dd, J = 1.91, 4.26 Hz, 1H), 2.69 (t, J = 7.34 Hz, 2H), 1.68 (quin, J = 7.56 Hz, 2H), 1.31-1.40 (m, 6H), 0.90 (t, J = 7.34 Hz, 3H) |

TABLE 6-continued

| Intermediate number | IUPAC name | starting material | $^1$H NMR δ (ppm) for Intermediate |
|---|---|---|---|
| 80 | 5-(4-hexyl-3-propylphenyl)-6-(2-thienyl)pyridin-2-carbaldehyde | Intermediate 57 | $^1$H NMR (300 MHz, CDCl$_3$) δ 10.10 (s, 1H), 7.81 (d, J = 7.91 Hz, 1H), 7.69 (d, J = 7.62 Hz, 1H), 7.28 (d, J = 4.98 Hz, 1H), 7.19 (d, J = 7.62 Hz, 1H), 7.04-7.09 (m, 2H), 6.80 (t, J = 4.40 Hz, 1H), 6.70 (d, J = 3.81 Hz, 1H), 2.65 (dd, J = 6.74, 7.91 Hz, 2H), 2.58 (dd, J = 7.62, 8.50 Hz, 2H), 1.57 (s, 4H), 1.24-1.44 (m, 6H), 0.84-0.95 (m, 6H) |
| 81 | 5-[4-(3-phenylpropyl)phenyl]-6-(2-thienyl)pyridin-2-carbaldehyde | Intermediate 58 | $^1$H NMR (600 MHz, CDCl$_3$) δ 10.15 (d, J = 0.59 Hz, 1H), 7.86 (d, J = 7.63 Hz, 1H), 7.73 (dd, J = 0.73, 7.78 Hz, 1H), 7.20-7.33 (m, 10H), 6.85 (dd, J = 3.81, 4.99 Hz, 1H), 6.74 (dd, J = 0.88, 3.81 Hz, 1H), 2.75 (t, J = 7.92 Hz, 2H), 2.71 (t, J = 7.63 Hz, 2H), 2.01-2.06 (m, 2H) |
| 82 | 5-(4-hexylphenyl)-6-(1,3-oxazol-4-yl)pyridin-2-carbaldehyde | Intermediate 59 | $^1$H NMR (300 MHz, CDCl$_3$) δ 10.26 (s, 1H), 7.97 (d, J = 7.62 Hz, 1H), 7.90 (s, 1H), 7.81 (d, J = 7.91 Hz, 1H), 7.19-7.29 (m, 4H), 7.07 (s, 1H), 2.68 (t, J = 7.77 Hz, 2H), 1.61-1.72 (m, 2H), 1.22-1.41 (m, 6H), 0.83-0.95 (m, 3H) |
| 83 | 5-(4-hexylphenyl)-6-(1,3-thiazol-2-yl)pyridin-2-carbaldehyde | Intermediate 60 | $^1$H NMR (300 MHz, CDCl$_3$) δ 10.19 (s, 1H), 7.98-8.07 (m, J = 8.50 Hz, 1H), 7.90 (d, J = 8.21 Hz, 1H), 7.75 (d, J = 2.93 Hz, 1H), 7.39 (d, J = 3.22 Hz, 1H), 7.19-7.24 (m, 4H), 2.66 (t, J = 7.62 Hz, 2H), 1.58-1.70 (m, 2H), 1.25-1.40 (m, 6H), 0.90 (t, J = 6.01 Hz, 3H) |
| 84 | 6-(2-furyl)-5-(4-hexylphenyl)pyridin-2-carbaldehyde | Intermediate 61 | $^1$H NMR (300 MHz, CDCl$_3$) δ 10.20 (s, 1H), 7.89 (d, J = 7.62 Hz, 1H), 7.76 (d, J = 7.91 Hz, 1H), 7.46 (s, 1H), 7.19-7.27 (m, 4H), 6.33 (dd, J = 1.61, 3.37 Hz, 1H), 6.12 (d, J = 3.22 Hz, 1H), 2.68 (t, J = 7.62 Hz, 2H), 1.61-1.73 (m, 2H), 1.25-1.42 (m, 6H), 0.90 (t, J = 6.30 Hz, 3H) |

Example 16

Compound 1

(3-{[6-(5-Hexyl-pyridin-2-yl)-biphenyl-3-ylmethyl]-amino}-propyl)-phosphonic acid

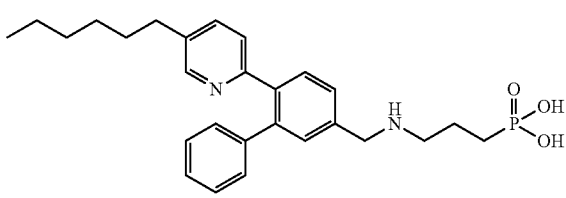 [SMILES: CCCCCCc1ccc(-c2ccc(CNCCCP(=O)(O)O)cc2-c2ccccc2)nc1]

To a solution of 6-(5-hexylpyridin-2-yl)biphenyl-3-carbaldehyde (80 mg, 0.233 mmol) and (3-aminopropyl)phosphonic acid (32.4 mg) in methanol was added tetrabutylammonium hydroxide (1M in MeOH, 0.23 mL). The reaction mixture was heated to 50° C. for 30 min with stirring, then sodium cyanoborohydride (41 mg, 0.65 mmol) was added. The reaction mixture was heated to 50° C. with stirring for 3 h. After cooling to RT, the mixture was concentrated and purified by MPLC (0-100% ethyl acetate in hexanes) to give 36 mg of the desired product as a colorless solid. $^1$H NMR (300 MHz, CD$_3$OD) δ 8.34 (d, J=1.76 Hz, 1H), 7.58-7.63 (m, 3H), 7.41 (dd, J=2.34, 8.20 Hz, 1H), 7.20-7.25 (m, 3H), 7.11-7.16 (m, 2H), 6.91 (d, J=7.91 Hz, 1H), 4.21 (s, 2H), 3.11 (t, J=6.30 Hz, 2H), 2.61 (t, J=7.62 Hz, 2H), 1.92-2.07 (m, 2H), 1.55-1.74 (m, 4H), 1.31 (br. s., 6H), 0.86-0.92 (m, 3H).

Compounds 2-28 were prepared from the corresponding starting materials, in a similar manner to the method described in Example 16 for Compound 1. The starting materials and the results are described below in Table 7.

TABLE 7

| Comp No. | IUPAC name | starting material | ¹H NMR δ (ppm) for Compound |
|---|---|---|---|
| 2 | (3-{[5-(4-Hexyl-phenyl)-6-thiophen-2-yl-pyridin-2-ylmethyl]-amino}-propyl)-phosphonic acid | Interm 78 | ¹H NMR (300 MHz, CD₃OD) δ 7.66 (d, J = 7.91 Hz, 1H), 7.35-7.39 (m, 2H), 7.17-7.27 (m, 4H), 6.80 (t, J = 4.25 Hz, 1H), 6.68 (d, J = 3.81 Hz, 1H), 4.30 (s, 2H), 3.17-3.26 (m, 2H), 2.68 (t, J = 7.62 Hz, 2H), 1.98-2.12 (m, 2H), 1.61-1.77 (m, 4H), 1.28-1.48 (m, 6H), 0.91 (t, J = 6.74 Hz, 3H) |
| 3 | (3-{[6-(5-Fluoro-thiophen-2-yl)-5-(4-hexyl-phenyl)-pyridin-2-ylmethyl]-amino}-propyl)-phosphonic acid | Interm 79 | ¹H NMR (300 MHz, CD₃OD) δ 7.68 (d, J = 7.91 Hz, 1H), 7.41 (d, J = 7.91 Hz, 1H), 7.26-7.37 (m, 4H), 6.35 (dd, J = 3.80 Hz, 1H), 6.30 (dd, J = 1.76, 4.10 Hz, 1H), 4.36 (s, 2H), 3.26 (t, J = 6.15 Hz, 2H), 2.75 (t, J = 7.47 Hz, 2H), 2.03-2.18 (m, 2H), 1.66-1.82 (m, 4H), 1.37-1.53 (m, 6H), 0.96 (t, J = 6.74 Hz, 3H) |
| 4 | (3-{[5-(4-Hexyl-3-propyl-phenyl)-6-thiophen-2-yl-pyridin-2-ylmethyl]-amino}-propyl)-phosphonic acid | Interm 80 | ¹H NMR (300 MHz, CD₃OD) δ 7.64 (d, J = 7.62 Hz, 1H), 7.34-7.38 (m, 2H), 7.21 (d, J = 8.50 Hz, 1H), 7.05 (br. s., 2H), 6.79 (t, J = 4.40 Hz, 1H), 6.67 (d, J = 3.52 Hz, 1H), 4.23 (s, 2H), 3.12 (t, J = 6.30 Hz, 2H), 2.69 (t, J = 7.77 Hz, 2H), 2.60 (t, J = 7.47 Hz, 2H), 1.95-2.09 (m, 2H), 1.52-1.75 (m, 6H), 1.30-1.48 (m, 6H), 0.93 (t, J = 7.03 Hz, 6H) |
| 5 | [3-({5-[4-(3-Phenyl-propyl)-phenyl]-6-thiophen-2-yl-pyridin-2-ylmethyl}-amino)-propyl]-phosphonic acid | Interm 81 | ¹H NMR (300 MHz, CD₃OD) δ 7.68 (d, J = 7.91 Hz, 1H), 7.35-7.39 (m, 2H), 7.15-7.30 (m, 9H), 6.81 (t, J = 4.54 Hz, 1H), 6.70 (d, J = 3.81 Hz, 1H), 4.29 (s, 2H), 3.19 (t, J = 6.74 Hz, 2H), 2.63-2.75 (m, 4H), 1.95-2.09 (m, 4H), 1.66-1.77 (m, 2H) |
| 6 | (3-{[5-(4-Hexyl-phenyl)-6-thiophen-3-yl-pyridin-2-ylmethyl]-amino}-propyl)-phosphonic acid | Interm 63 | ¹H NMR (300 MHz, CD₃OD) δ 7.74 (d, J = 7.91 Hz, 1H), 7.42 (d, J = 8.21 Hz, 1H), 7.40 (d, J = 2.93 Hz, 1H), 7.11-7.23 (m, 5H), 7.05 (d, J = 4.98 Hz, 1H), 4.31 (s, 2H), 3.16 (t, J = 6.45 Hz, 2H), 2.64 (t, J = 7.62 Hz, 2H), 2.03 (dt, J = 6.78, 16.92 Hz, 2H), 1.58-1.76 (m, 4H), 1.29-1.45 (m, 6H), 0.90 (t, J = 6.15 Hz, 3H) |

TABLE 7-continued

| Comp No. | IUPAC name | starting material | $^1$H NMR δ (ppm) for Compound |
|---|---|---|---|
| 7 | (3-{[5-(4-Hexyl-phenyl)-6-oxazol-4-yl-pyridin-2-ylmethyl]-amino}-propyl)-phosphonic acid | Interm 82 | $^1$H NMR (600 MHz, CD$_3$OD) δ 8.31 (d, J = 0.88 Hz, 1H), 7.75 (d, J = 7.63 Hz, 1H), 7.49 (d, J = 7.63 Hz, 1H), 7.33 (d, J = 8.22 Hz, 2H), 7.20 (d, J = 7.92 Hz, 2H), 6.88 (s, 1H), 4.39 (s, 2H), 3.19 (t, J = 6.75 Hz, 2H), 2.71 (t, J = 7.63 Hz, 2H), 2.07 (ddtd, J = 6.46, 7.04, 7.63, 17.02 Hz, 2H), 1.63-1.75 (m, 4H), 1.32-1.45 (m, 6H), 0.91 (t, J = 7.04 Hz, 3H) |
| 8 | (3-{[5-(4-Hexyl-phenyl)-6-thiazol-2-yl-pyridin-2-ylmethyl]-amino}-propyl)-phosphonic acid | Interm 83 | $^1$H NMR (600 MHz, CD$_3$OD) δ 7.83 (d, J = 7.92 Hz, 1H), 7.74 (d, J = 3.23 Hz, 1H), 7.60 (s, 1H), 7.58 (d, J = 7.92 Hz, 1H), 7.21 (d, J = 8.22 Hz, 2H), 7.17 (d, J = 7.92 Hz, 2H), 4.24 (s, 2H), 3.05 (t, J = 6.60 Hz, 2H), 2.65 (dd, J = 7.60 Hz, 1H), 1.96-2.03 (m, 2H), 1.62-1.71 (m, 4H), 1.29-1.45 (m, 6H), 0.89-0.93 (m, 3H) |
| 9 | (3-{[6-Furan-2-yl-5-(4-hexyl-phenyl)-pyridin-2-ylmethyl]-amino}-propyl)-phosphonic acid | Interm 84 | $^1$H NMR (300 MHz, CD$_3$OD) δ 7.70 (d, J = 7.91 Hz, 1H), 7.45 (s, 2H), 7.24 (d, J = 7.62 Hz, 2H), 7.15 (d, J = 8.20 Hz, 2H), 6.35-6.38 (m, J = 1.76 Hz, 1H), 6.26 (d, J = 2.93 Hz, 1H), 4.34 (s, 2H), 3.20 (t, J = 6.30 Hz, 2H), 2.67 (t, J = 7.62 Hz, 2H), 1.98-2.12 (m, 2H), 1.61-1.78 (m, 4H), 1.27-1.46 (m, 6H), 0.91 (t, J = 6.01 Hz, 3H) |
| 10 | (3-{[5-(4-Hexyl-phenyl)-6-(3-hydroxy-phenyl)-pyridin-2-ylmethyl]-amino}-propyl)-phosphonic acid | Interm 69 | $^1$H NMR (300 MHz, CD$_3$OD) δ 7.83 (d, J = 7.91 Hz, 1H), 7.48 (d, J = 7.91 Hz, 1H), 7.10 (s, 4H), 7.02 (s, 1H), 6.98 (d, J = 7.62 Hz, 1H), 6.68 (d, J = 8.20 Hz, 2H), 4.34 (s, 2H), 3.17-3.23 (m, 2H), 2.59 (t, J = 7.62 Hz, 2H), 1.96-2.09 (m, 2H), 1.55-1.76 (m, 4H), 1.27-1.48 (m, 6H), 1.02 (t, J = 7.33 Hz, 3H) |
| 11 | (3-{[4-(3,3,4,4,5,5,6,6,6-Nonafluoro-hexyl)-[1,1';2',1″]terphenyl-4'-ylmethyl]-amino}-propyl)-phosphonic acid | Interm 73 | $^1$H NMR (300 MHz, CD$_3$OD) δ 7.52-7.58 (m, 2H), 7.45 (d, J = 7.33 Hz, 1H), 7.05-7.22 (m, 9H), 4.18 (s, 2H), 3.12 (t, J = 6.15 Hz, 2H), 2.84-2.91 (m, 2H), 2.33-2.52 (m, 2H), 1.92-2.07 (m, 2H), 1.61-1.74 (m, 2H) |

TABLE 7-continued

| Comp No. | IUPAC name | starting material | $^1$H NMR δ (ppm) for Compound |
|---|---|---|---|
| 12 | (3-{[4-(3-Phenyl-propyl)-[1,1';2',1'']terphenyl-4'-ylmethyl]-amino}-propyl)-phosphonic acid | Interm 67 | $^1$H NMR (300 MHz, CD$_3$OD) δ 7.56 (d, J = 1.76 Hz, 1H), 7.53 (s, 1H), 7.45 (d, J = 7.33 Hz, 1H), 7.10-7.27 (m, 10H), 6.97-7.04 (m, 4H), 4.18 (s, 2H), 3.12 (t, J = 6.30 Hz, 2H), 2.57 (t, J = 7.62 Hz, 4H), 1.82-2.07 (m, 4H), 1.61-1.75 (m, 2H) |
| 13 | [3-({6-(3-Chloro-phenyl)-5-[4-(3-phenyl-propyl)-phenyl]-pyridin-2-ylmethyl}-amino)-propyl]-phosphonic acid | Interm 72 | $^1$H NMR (300 MHz, CD$_3$OD) δ 7.86 (d, J = 7.91 Hz, 1H), 7.54 (d, J = 7.91 Hz, 1H), 7.38-7.40 (m, 1H), 7.07-7.30 (m, 12H), 4.24 (s, 2H), 3.06 (t, J = 6.45 Hz, 2H), 2.62 (dt, J = 7.66, 9.89 Hz, 4H), 1.94 (d, J = 7.33 Hz, 4H), 1.60-1.73 (m, 2H) |
| 14 | [3-({6-Phenyl-5-[4-(3-phenyl-propyl)-phenyl]-pyridin-2-ylmethyl}-amino)-propyl]-phosphonic acid | Interm 68 | $^1$H NMR (300 MHz, CD$_3$OD) δ 7.84 (d, J = 7.91 Hz, 1H), 7.52 (d, J = 7.91 Hz, 1H), 7.34-7.39 (m, 2H), 7.20-7.27 (m, 5H), 7.05-7.16 (m, 7H), 4.34 (s, 2H), 3.17 (t, J = 6.74 Hz, 2H), 2.56-2.64 (m, 4H), 1.85-2.10 (m, 4H), 1.62-1.75 (m, 2H) |
| 15 | (3-{[6-(3-Chloro-phenyl)-5-(4-hexyl-3-propyl-phenyl)-pyridin-2-ylmethyl]-amino}-propyl)-phosphonic acid | Interm 71 | $^1$H NMR (300 MHz CD$_3$OD) δ 7.87 (d, J = 7.91 Hz, 1H), 7.54 (d, J = 7.91 Hz, 1H), 7.35-7.37 (m, 1H), 7.30 (tt, J = 1.87, 6.63 Hz, 1H), 7.19-7.26 (m, 2H), 7.12 (d, J = 7.91 Hz, 1H), 6.99 (dd, J = 1.90, 7.76 Hz, 1H), 6.86 (d, J = 2.05 Hz, 1H), 4.35 (s, 2H), 3.18 (t, J = 7.60 Hz, 2H), 2.61 (t, J = 8.20 Hz, 2H), 2.49 (t, J = 7.90 Hz, 2H), 1.95-2.09 (m, 2H), 1.62-1.75 (m, 4H), 1.50-1.61 (m, 2H), 1.29-1.48 (m, 6H), 0.90 (t, J = 6.40 Hz, 3H), 0.84 (t, J = 7.30 Hz, 3H) |

TABLE 7-continued

| Comp No. | IUPAC name | starting material | $^1$H NMR δ (ppm) for Compound |
|---|---|---|---|
| 16 | (3-{[5-(4-Hexyl-3-propyl-phenyl)-6-phenyl-pyridin-2-ylmethyl]-amino}-propyl)-phosphonic acid | Interm 70 | $^1$H NMR (300 MHz, CD$_3$OD) δ 7.86 (d, J = 7.91 Hz, 1H), 7.50 (d, J = 7.91 Hz, 1H), 7.35-7.39 (m, 2H), 7.22-7.27 (m, 3H), 7.09 (d, J = 7.91 Hz, 1H), 6.99 (dd, J = 1.80, 7.91 Hz, 1H), 6.85 (d, J = 1.76 Hz, 1H), 4.35 (s, 2H), 3.19 (t, J = 5.86 Hz, 3H), 2.59 (t, J = 8.20 Hz, 2H), 2.45 (t, J = 8.20 Hz, 2H), 1.95-2.09 (m, 2H), 1.48-1.75 (m, 6H), 1.30-1.46 (m, 6H), 0.91 (t, J = 6.15 Hz, 3H), 0.81 (t, J = 7.33 Hz, 3H) |
| 17 | (3-{[6-(3-Fluoro-phenyl)-5-(4-pentyloxy-phenyl)-pyridin-2-ylmethyl]-amino}-propyl)-phosphonic acid | Interm 75 | $^1$H NMR (300 MHz, CD$_3$OD) δ 7.84 (d, J = 7.91 Hz, 1H), 7.52 (d, J = 7.91 Hz, 1H), 7.06-7.28 (m, 5H), 6.97-7.04 (m, 1H), 6.85 (d, J = 8.79 Hz, 2H), 4.29 (s, 2H), 3.96 (t, J = 6.45 Hz, 2H), 3.12 (t, J = 6.45 Hz, 2H), 1.92-2.08 (m, 2H), 1.60-1.82 (m, 4H), 1.35-1.49 (m, 4H), 0.94 (t, J = 7.03 Hz, 3H) |
| 18 | (3-{[6-(4-Fluoro-phenyl)-5-(4-pentyloxy-phenyl)-pyridin-2-ylmethyl]-amino}-propyl)-phosphonic acid | Interm 76 | $^1$H NMR (300 MHz, CD$_3$OD) δ 7.82 (d, J = 7.91 Hz, 1H), 7.49 (d, J = 7.91 Hz, 1H), 7.38-7.45 (m, 2H), 6.95-7.10 (m, 4H), 6.84 (d, J = 8.79 Hz, 2H), 4.29 (s, 2H), 3.95 (t, J = 6.45 Hz, 2H), 3.13 (t, J = 6.45 Hz, 2H), 1.93-2.08 (m, 2H), 1.60-1.81 (m, 4H), 1.33-1.51 (m, 4H), 0.94 (t, J = 7.00 Hz, 3H) |
| 19 | (3-{[5-(4-Pentyloxy-phenyl)-6-phenyl-pyridin-2-ylmethyl]-amino}-propyl)-phosphonic acid | Interm 74 | $^1$H NMR (300 MHz, CD$_3$OD) δ 7.83 (d, J = 7.91 Hz, 1H), 7.50 (d, J = 7.91 Hz, 1H), 7.36-7.40 (m, 2H), 7.23-7.28 (m, 3H), 7.03-7.08 (m, 2H), 6.78-6.83 (m, 2H), 4.33 (s, 2H), 3.93 (t, J = 6.45 Hz, 2H), 3.17 (t, J = 6.59 Hz, 2H), 1.94-2.09 (m, 2H), 1.61-1.80 (m, 4H), 1.33-1.50 (m, 4H), 0.94 (t, J = 7.00 Hz, 3H) |

TABLE 7-continued

| Comp No. | IUPAC name | starting material | ¹H NMR δ (ppm) for Compound |
|---|---|---|---|
| 20 | (3-{[6-(6-Octyl-pyridin-3-yl)-biphenyl-3-ylmethyl]-amino}-propyl)-phosphonic acid | Interm 66 | ¹H NMR (300 MHz, CD₃OD) δ 8.10 (dd, J = 0.59, 2.34 Hz, 1H), 7.63 (dd, J = 2.05, 7.91 Hz, 1H), 7.59 (d, J = 1.47 Hz, 1H), 7.50 (dd, J = 2.05, 8.20 Hz, 2H), 7.12-7.27 (m, 6H), 4.19 (s, 2H), 3.10 (t, J = 6.15 Hz, 2H), 2.72 (t, J = 7.90 Hz, 2H), 1.93-2.08 (m, 2H), 1.61-1.74 (m, 4H), 1.30 (s, 6H), 0.89 (t, J = 6.54 Hz, 3H) |
| 21 | {3-[(4-Octyl-[1,1';2',1'']terphenyl-4'-ylmethyl)-amino]-propyl}-phosphonic acid | Interm 77 | ¹H NMR (300 MHz, CD₃OD) δ 7.53 (s, 2H), 7.41-7.47 (m, 1H), 7.10-7.20 (m, 5H), 6.95-7.05 (m, 4H), 4.16 (d, J = 9.38 Hz, 2H), 3.04-3.14 (m, 2H), 2.54 (t, J = 7.33 Hz, 2H), 1.93-2.05 (m, 2H), 1.53-1.74 (m, 4H), 1.26-1.48 (m, 6H), 0.89 (t, J = 7.00 Hz, 3H) |
| 22 | (3-{[6-(6-Octyl-pyridin-3-yl)-biphenyl-3-ylmethyl]-amino}-propyl)-phosphonic acid | | ¹H NMR (300 MHz, CD₃OD) δ 8.09 (d, J = 1.76 Hz, 1H), 7.59-7.65 (m, 2H), 7.47-7.52 (m, 2H), 7.11-7.26 (m, 6H), 4.20 (s, 2H), 3.12 (t, J = 6.01 Hz, 2H), 2.72 (t, J = 7.62 Hz, 2H), 1.93-2.11 (m, 2H), 1.60-1.76 (m, 4H), 1.29 (d, J = 3.22 Hz, 10H), 0.89 (t, J = 6.74 Hz, 3H) |
| 23 | Phosphoric acid mono-{2-[(4-hexyl[1,1';2',1'']terphenyl-4'-ylmethyl)-amino]ethyl} ester | Interm 62 | ¹H NMR (300 MHz, CD₃OD) δ 7.56 (dd, J = 2.05, 7.91 Hz, 1H), 7.52 (s, 1H), 7.42 (d, J = 7.62 Hz, 1H), 7.10-7.20 (m, 5H), 6.95-7.02 (m, 4H), 4.21 (s, 2H), 4.07-4.14 (m, 2H), 3.16-3.19 (m, 2H), 2.54 (t, J = 7.60 Hz, 2H), 1.51-1.71 (m, 2H), 1.26-1.33 (m, 6H), 0.89 (t, J = 6.74 Hz, 3H) |
| 25 | [1-(4-Hexyl-[1,1';2',1'']terphenyl-4'-ylmethyl)-pyrrolidin-3-yl]-phosphonic acid | Interm 62 | ¹H NMR (300 MHz, CD₃OD) δ 7.35-7.44 (m, 3H), 7.10-7.19 (m, 5H), 7.00 (s, 4H), 3.79-3.91 (m, 2H), 3.14-3.23 (m, 1H), 2.97-3.04 (m, 1H), 2.61-2.78 (m, 2H), 2.55 (t, J = 7.62 Hz, 2H), 2.30-2.44 (m, 1H), 2.06-2.19 (m, 2H), 1.52-1.61 (m, 2H), 1.30 (s, 6H), 0.89 (t, J = 6.45 Hz, 3H) |

TABLE 7-continued

| Comp No. | IUPAC name | starting material | $^1$H NMR δ (ppm) for Compound |
|---|---|---|---|
| 26 | [1-(4-Hexyl-[1,1';2',1"]terphenyl-4'-ylmethyl)-pyrrolidin-3-yl]-phosphonic acid monoethyl ester | Interm 62 | $^1$H NMR (300 MHz, CD$_3$OD) δ 7.40-7.49 (m, 3H), 7.16-7.21 (m, 3H), 7.10-7.14 (m, 2H), 7.00 (s, 4H), 4.09 (s, 2H), 3.92 (quin, J = 7.00 Hz, 2H), 3.35 (s, 1H), 3.14-3.23 (m, 1H), 2.90-3.02 (m, 2H), 2.39-2.58 (m, 3H), 2.10-2.23 (m, 2H), 1.52-1.61 (m, 2H), 1.27-1.34 (m, 6H), 1.23 (t, J = 7.03 Hz, 3H), 0.88 (t, J = 7.00 Hz, 3H) |
| 27 | (3-{[5-(4-Hexyl-phenyl)-6-phenyl-pyridin-2-ylmethyl]-amino}-propyl)-phosphonic acid | Interm 65 | $^1$H NMR (300 MHz, CD$_3$OD) δ 7.85 (d, J = 7.91 Hz, 1H), 7.51 (d, J = 7.91 Hz, 1H), 7.35-7.38 (m, 2H), 7.19-7.27 (m, 3H), 7.04-7.11 (m, 4H), 4.32 (s, 2H), 3.15 (t, J = 6.59 Hz, 2H), 2.59 (t, J = 7.62 Hz, 2H), 1.94-2.09 (m, 2H), 1.54-1.75 (m, 4H), 1.27-1.48 (m, 6H), 0.89 (t, J = 6.45 Hz, 3H) |
| 28 | (3-{[(4-hexyl-1,1':2',1"-terphenyl-4'-yl)methyl]amino}propyl)phosphonic acid | Interm 62 | $^1$H NMR (300 MHz, CD$_3$OD) δ 7.47-7.70 (m, 2H), 7.42 (d, J = 7.92 Hz, 1H), 7.05-7.28 (m, 5H), 6.88-7.05 (m, 4H), 4.17 (s, 2H), 3.11 (t, J = 6.45 Hz, 2H), 2.53 (t, J = 7.62 Hz, 2H), 1.86-2.10 (m, 2H), 1.46-1.79 (m, 4H), 1.16-1.41 (m, 6H), 0.70-0.95 (m, 3H). |

Example 16

Biological Data

Novel compounds were synthesized and tested for S1P1 activity using the GTP γ$^{35}$S binding assay. These compounds may be assessed for their ability to activate or block activation of the human S1P1 receptor in cells stably expressing the S1P1 receptor. GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a n-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 8 shows activity potency: S1P1 receptor from GTP γ$^{35}$S: nM, (EC$_{50}$), and stimulation (%).

Activity potency: S1P1 receptor from GTP γ$^{35}$S: nM, (EC$_{50}$)

TABLE 8

| Compound IUPAC name | GTPγ$^{35}$S EC50 (nM) | % STIMULATION @ 5 μM (%) |
|---|---|---|
| (3-{[6-(5-Hexyl-pyridin-2-yl)-biphenyl-3-ylmethyl]-amino}-propyl)-phosphonic acid | 316.74 | 79.40 |
| (3-{[6-(6-Hexyl-pyridin-3-yl)-biphenyl-3-ylmethyl]-amino}-propyl)-phosphonic acid | 833.01 | 94.70 |
| (3-{[5-(4-Hexyl-phenyl)-6-phenyl-pyridin-2-ylmethyl]-amino}-propyl)-phosphonic acid | 252.03 | 112.30 |
| (3-{[6-(6-Octyl-pyridin-3-yl)-biphenyl-3-ylmethyl]-amino}-propyl)-phosphonic acid | 771.47 | 89.70 |
| (3-{[5-(4-Pentyloxy-phenyl)-6-phenyl-pyridin-2-ylmethyl]-amino}-propyl)-phosphonic acid | 357.84 | 95.50 |
| (3-{[6-(4-Fluoro-phenyl)-5-(4-pentyloxy-phenyl)-pyridin-2-ylmethyl]-amino}-propyl)-phosphonic acid | 472.12 | 104.20 |
| (3-{[6-(3-Fluoro-phenyl)-5-(4-pentyloxy-phenyl)-pyridin-2-ylmethyl]-amino}-propyl)-phosphonic acid | 2200.43 | 83.90 |
| (3-{[4-(3-Phenyl-propyl)-[1,1';2',1"]terphenyl-4'-ylmethyl]-amino}-propyl)-phosphonic acid | 625.06 | 64.00 |

TABLE 8-continued

| Compound IUPAC name | GTPγ35S EC50 (nM) | % STIMULATION @ 5 µM (%) |
|---|---|---|
| (3-{[4-(3,3,4,4,5,5,6,6,6-Nonafluoro-hexyl)-[1,1';2',1'']terphenyl-4'-ylmethyl]-amino}-propyl)-phosphonic acid | 416.06 | 71.80 |
| (3-{[5-(4-Hexyl-3-propyl-phenyl)-6-phenyl-pyridin-2-ylmethyl]-amino}-propyl)-phosphonic acid | 29.59 | 73.10 |
| [3-({6-Phenyl-5-[4-(3-phenyl-propyl)-phenyl]-pyridin-2-ylmethyl}-amino)-propyl]-phosphonic acid | 93.84 | 86.60 |
| [3-({6-(3-Chloro-phenyl)-5-[4-(3-phenyl-propyl)-phenyl]-pyridin-2-ylmethyl}-amino)-propyl]-phosphonic acid | 2427.07 | 64.00 |
| (3-{[5-(4-Hexyl-phenyl)-6-thiophen-2-yl-pyridin-2-ylmethyl]-amino}-propyl)-phosphonic acid | 5.26 | 68.10 |
| (3-{[5-(4-Hexyl-phenyl)-6-thiophen-3-yl-pyridin-2-ylmethyl]-amino}-propyl)-phosphonic acid | 9.19 | 76.90 |
| (3-{[6-Furan-2-yl-5-(4-hexyl-phenyl)-pyridin-2-ylmethyl]-amino}-propyl)-phosphonic acid | 0.44 | 88.60 |
| (3-{[5-(4-Hexyl-phenyl)-6-oxazol-4-yl-pyridin-2-ylmethyl]-amino}-propyl)-phosphonic acid | 0.87 | 86.10 |
| (3-{[5-(4-Hexyl-phenyl)-6-thiazol-2-yl-pyridin-2-ylmethyl]-amino}-propyl)-phosphonic acid | 6.52 | 89.30 |
| [3-({5-[4-(3-Phenyl-propyl)-phenyl]-6-thiophen-2-yl-pyridin-2-ylmethyl}-amino)-propyl]-phosphonic acid | 2.36 | 91.10 |
| (3-{[5-(4-Hexyl-3-propyl-phenyl)-6-thiophen-2-yl-pyridin-2-ylmethyl]-amino}-propyl)-phosphonic acid | 7.72 | 79.10 |
| (3-{[6-(5-Fluoro-thiophen-2-yl)-5-(4-hexyl-phenyl)-pyridin-2-ylmethyl]-amino}-propyl)-phosphonic acid | 25.05 | 110.70 |

Example 17

Lymphopenia Assay in Mice

Test drugs are prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples are obtained by puncturing the submandibular skin with a Goldenrod animal lancet at 5, 24, 48, 72, and 96 hrs post drug application. Blood is collected into microvettes (SARSTEDT) containing EDTA tripotassium salt. Lymphocytes in blood samples are counted using a HEMAVET Multispecies Hematology System, HEMAVET HV950FS (Drew Scientific Inc.). (Hale, J. et al Bioorg. & Med. Chem. Lett. 14 (2004) 3351).

Figure 2:
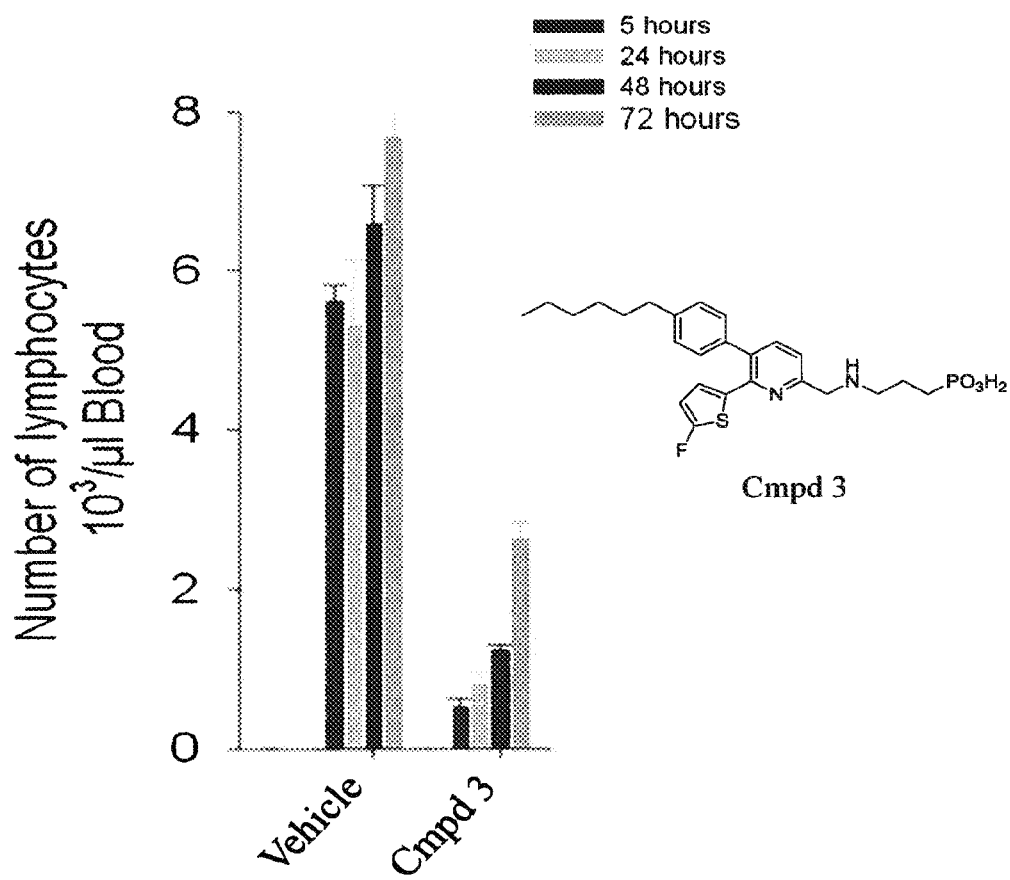
FIG. 2 shows the in vivo blood lymphocyte depletion after dosing the mice with Compound 3, (3-{[6-(5-Fluoro-thiophen-2-yl)-5-(4-hexyl-phenyl)-pyridin-2-ylmethyl]-amino}-propyl)-phosphonic acid.
Figure 3:
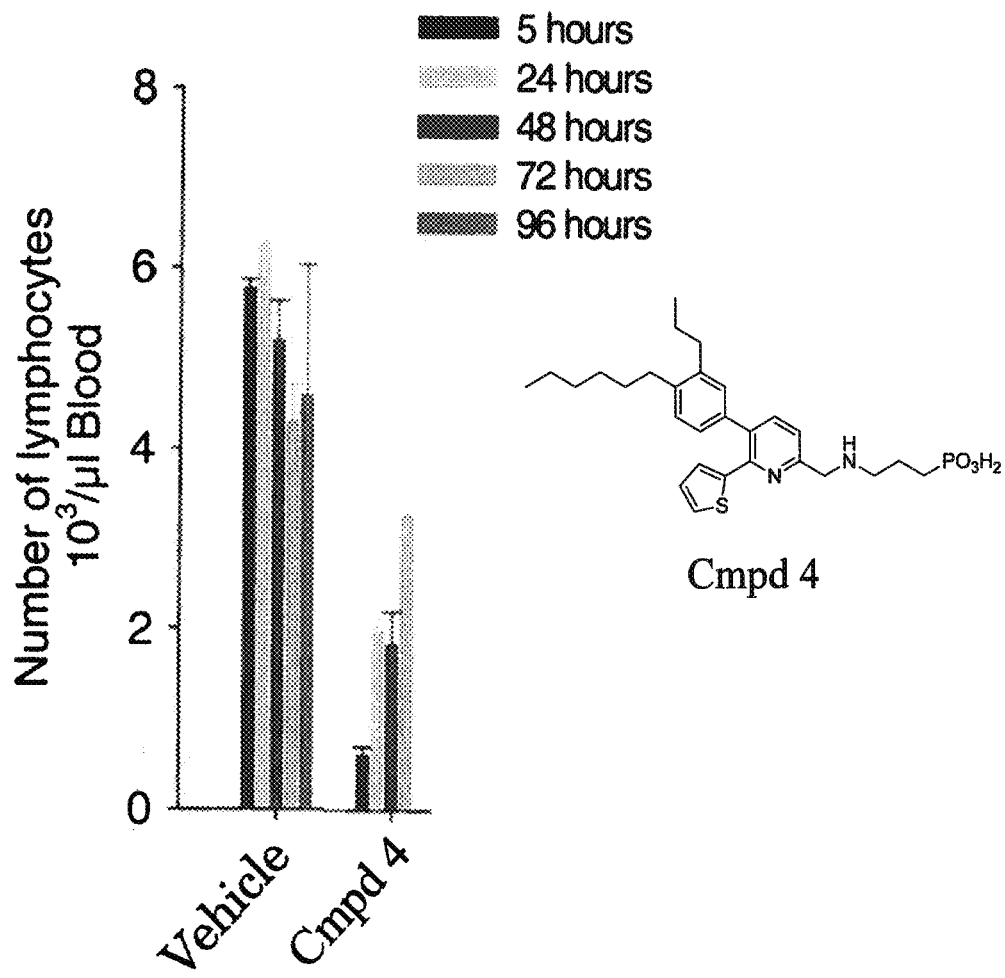
FIG. 3 shows the in vivo blood lymphocyte depletion after dosing the mice with Compound 4, (3-{[5-(4-Hexyl-3-propyl-phenyl)-6-thiophen-2-yl-pyridin-2-ylmethyl]-amino}-propyl)-phosphonic acid.
Figure 4:
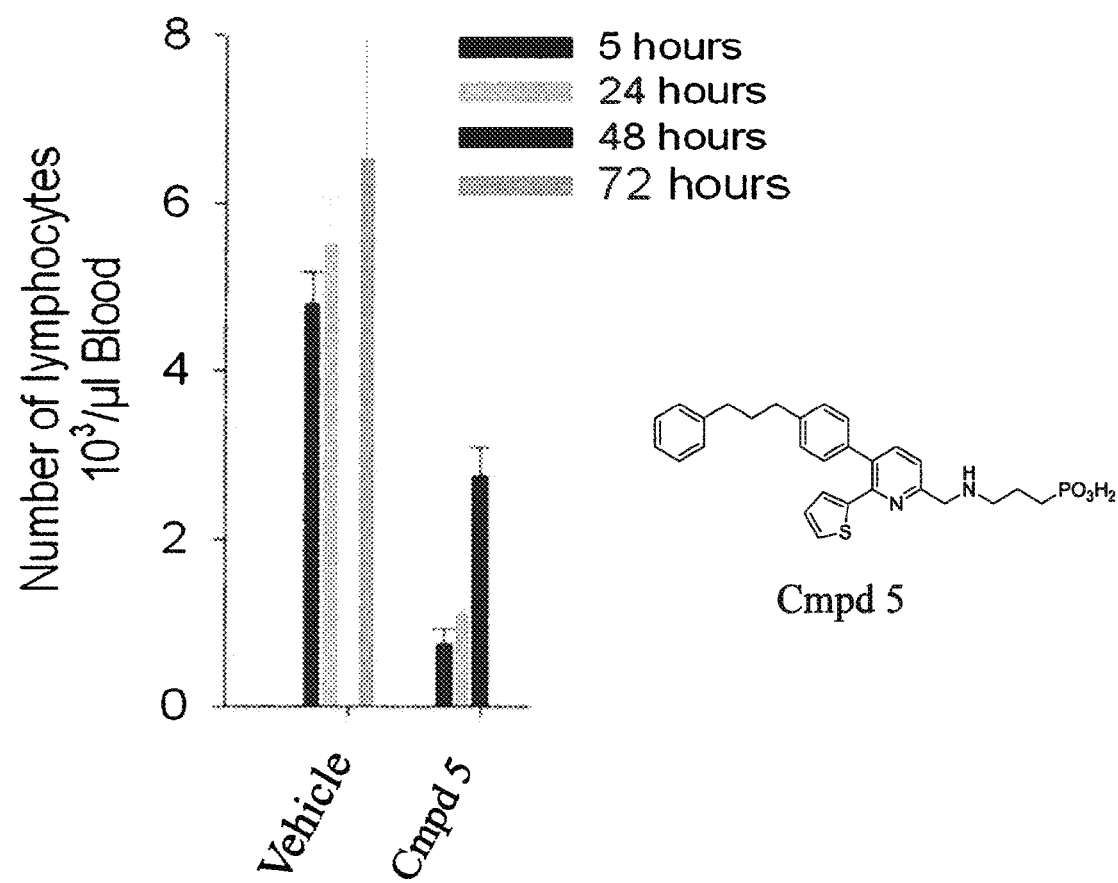
FIG. 4 shows the in vivo blood lymphocyte depletion after dosing the mice with Compound 5, [3-({5-[4-(3-Phenyl-propyl)-phenyl]-6-thiophen-2-yl-pyridin-2-ylmethyl}-amino)-propyl]-phosphonic acid.
Figure 5:
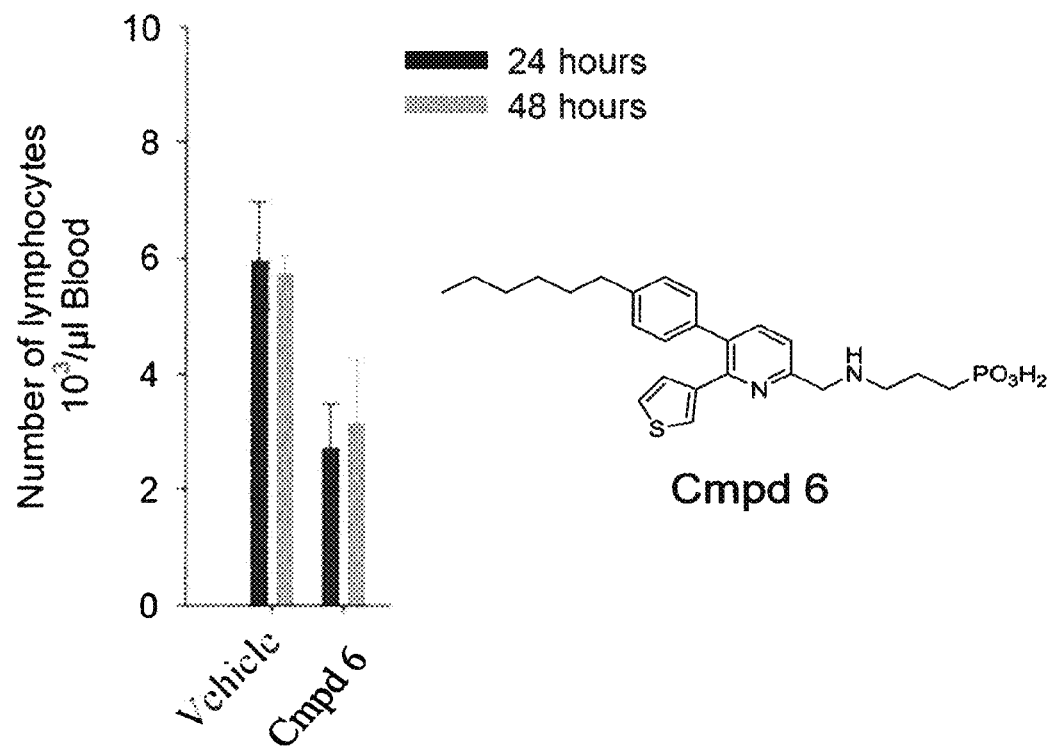
FIG. 5 shows the in vivo blood lymphocyte depletion after dosing the mice with Compound 6, (3-{[5-(4-Hexyl-phenyl)-6-thiophen-3-yl-pyridin-2-ylmethyl]-amino}-propyl)-phosphonic acid.
Figure 6:
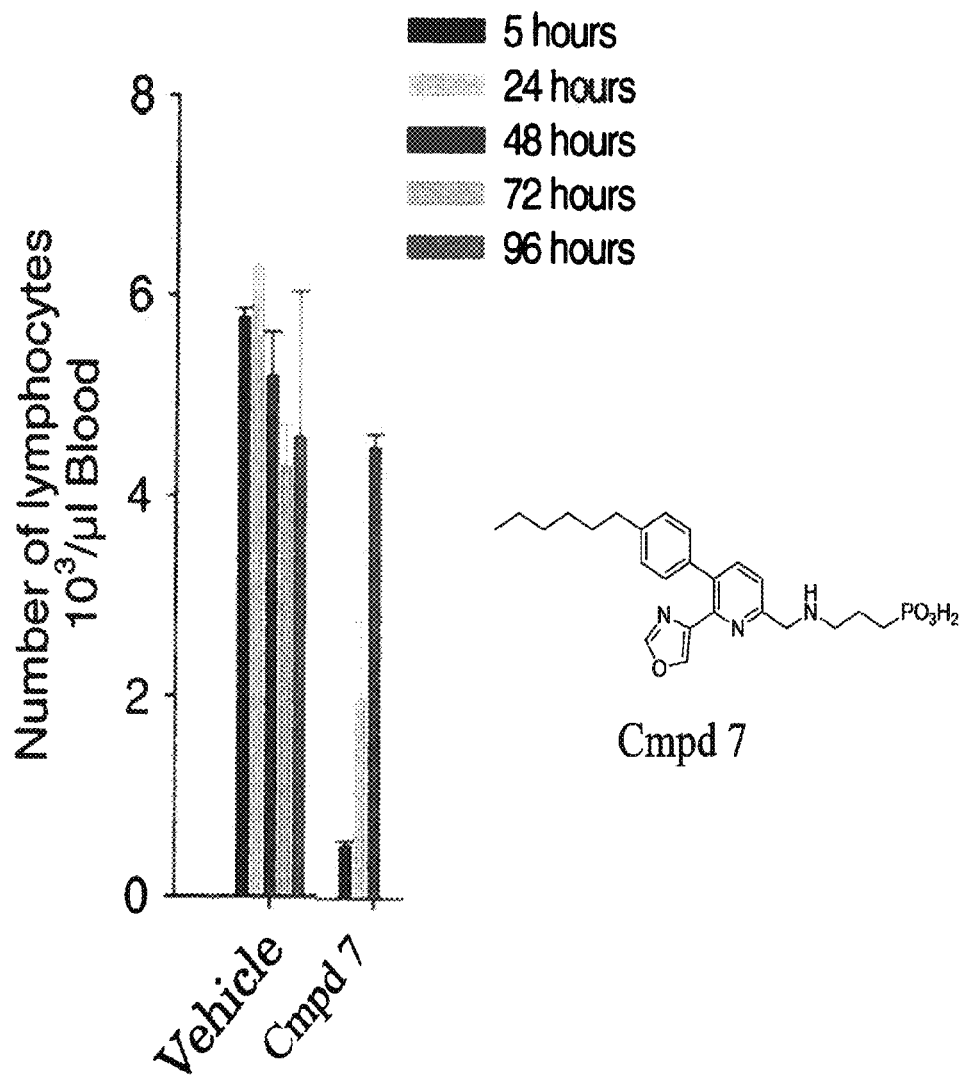
FIG. 6 shows the in vivo blood lymphocyte depletion after dosing the mice with Compound 7, (3-{[5-(4-Hexyl-phenyl)-6-oxazol-4-yl-pyridin-2-ylmethyl]-amino}-propyl)-phosphonic acid.
Figure 7:
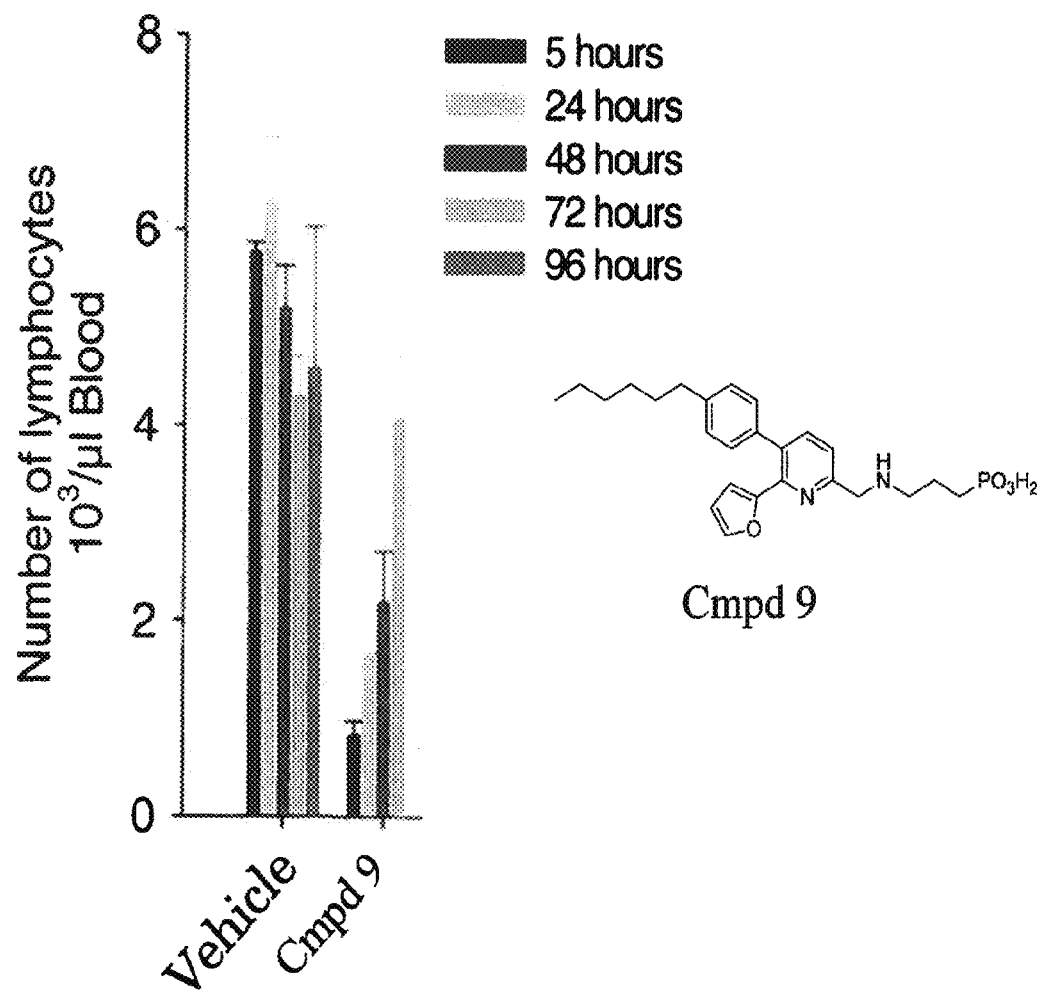
FIG. 7 shows the in vivo blood lymphocyte depletion after dosing the mice with Compound 9, (3-{[6-Furan-2-yl-5-(4-hexyl-phenyl)-pyridin-2-ylmethyl]-amino}-propyl)-phosphonic acid.
Figure 8:
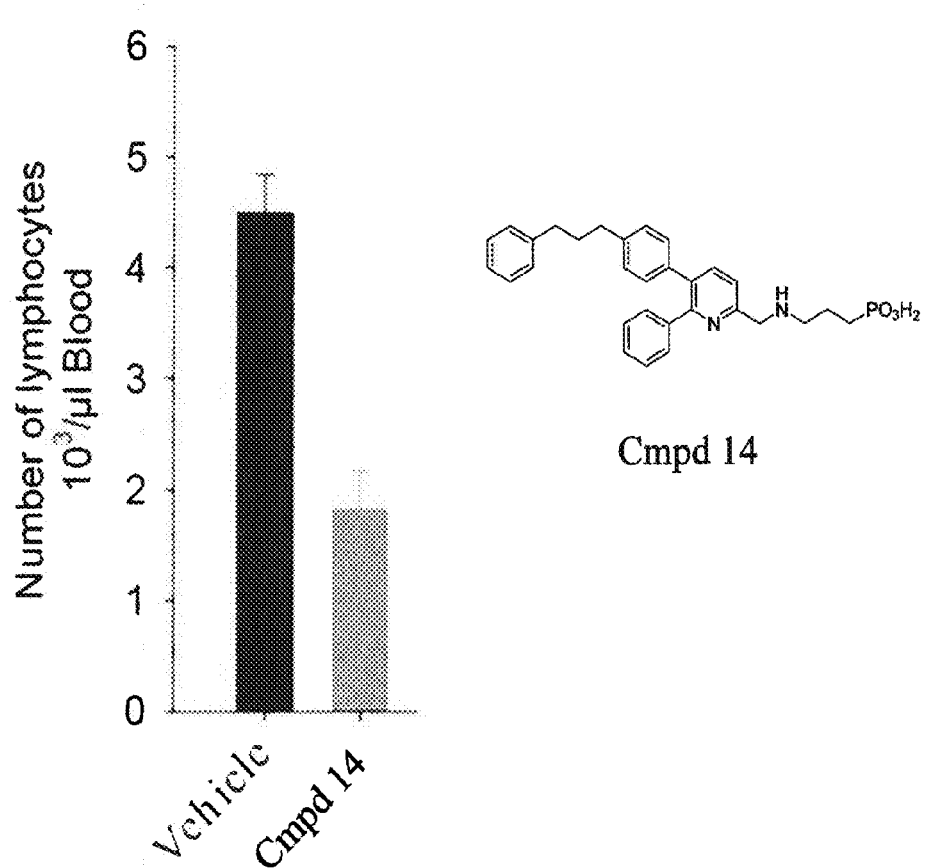
FIG. 8 shows the in vivo blood lymphocyte depletion after dosing the mice with Compound 14, [3-({6-Phenyl-5-[4-(3-phenyl-propyl)-phenyl]-pyridin-2-ylmethyl}-amino)-propyl]-phosphonic acid.
Figure 9:
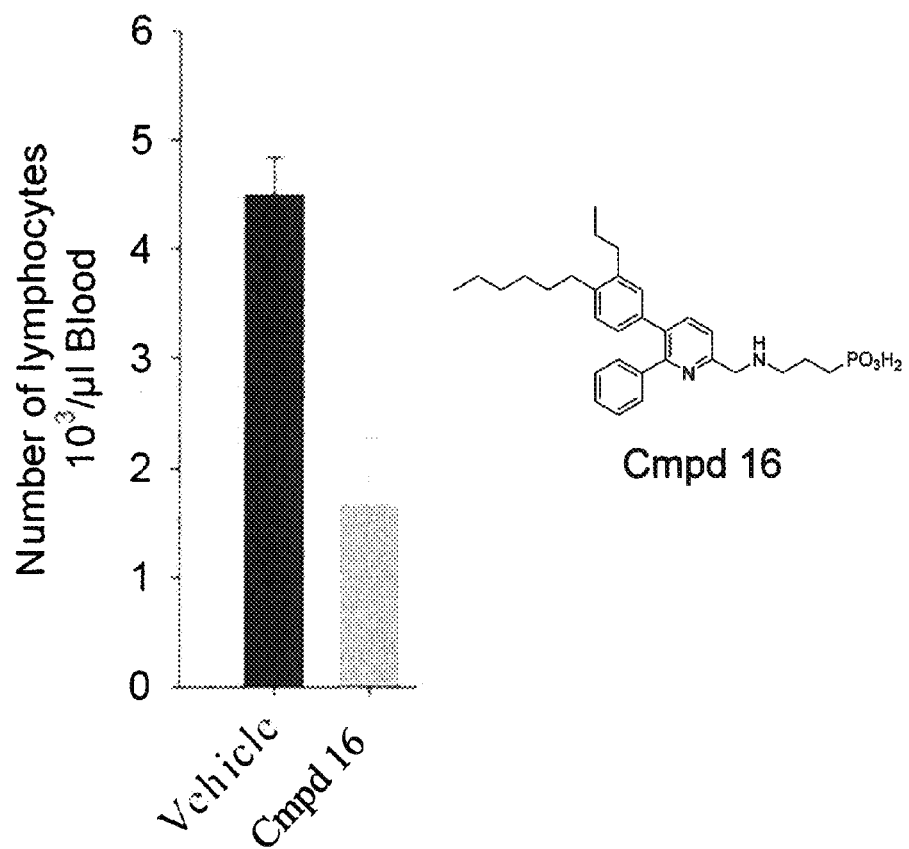
FIG. 9 shows the in vivo blood lymphocyte depletion after dosing the mice with Compound 16, (3-{[5-(4-Hexyl-3-propyl-phenyl)-6-phenyl-pyridin-2-ylmethyl]-amino}-propyl)-phosphonic acid.

A lymphopenia assay in mice; as previously described, was employed to measure the in vivo blood lymphocyte depletion after dosing with:

(3-{[5-(4-Hexyl-phenyl)-6-thiophen-2-yl-pyridin-2-ylmethyl]-amino}-propyl)-phosphonic acid, Compound 2 (FIG. 1);

(3-{[6-(5-Fluoro-thiophen-2-yl)-5-(4-hexyl-phenyl)-pyridin-2-ylmethyl]-amino}-propyl)-phosphonic acid, Compound 3 (FIG. 2);

(3-{[5-(4-Hexyl-3-propyl-phenyl)-6-thiophen-2-yl-pyridin-2-ylmethyl]-amino}-propyl)-phosphonic acid, Compound 4 (FIG. 3);

[3-({5-[4-(3-Phenyl-propyl)-phenyl]-6-thiophen-2-yl-pyridin-2-ylmethyl}-amino)-propyl]-phosphonic acid, Compound 5 (FIG. 4);

(3-{[5-(4-Hexyl-phenyl)-6-thiophen-3-yl-pyridin-2-ylmethyl]-amino}-propyl)-phosphonic acid, Compound 6 (FIG. 5);

(3-{[5-(4-Hexyl-phenyl)-6-oxazol-4-yl-pyridin-2-ylmethyl]-amino}-propyl)-phosphonic acid, Compound 7 (FIG. 6);

(3-{[6-Furan-2-yl-5-(4-hexyl-phenyl)-pyridin-2-ylmethyl]-amino}-propyl)-phosphonic acid, Compound 9 (FIG. 7);

[3-({6-Phenyl-5-[4-(3-phenyl-propyl)-phenyl]-pyridin-2-ylmethyl}-amino)-propyl]-phosphonic acid, Compound 14 (FIGS. 8) and (3-{[5-(4-Hexyl-3-propyl-phenyl)-6-phenyl-pyridin-2-ylmethyl]-amino}-propyl)-phosphonic acid, Compound 16 (FIG. 9).

The number of lymphocytes found in the blood was reduced by Compound 14 and Compound 16 after 5 h of drug application.

The number of lymphocytes found in the blood was reduced by Compound 2 and Compound 7 after 24 h of drug application.

The number of lymphocytes found in the blood was reduced by Compound 6, Compound 5 and Compound 9 after 48 h of drug application.

The number of lymphocytes found in the blood was reduced by Compound 3 and Compound 4 after 72 h of drug application.

These S1P agonist (or modulator) is useful for S1P-related diseases, and exemplified by the lymphopenia in vivo response. In general, test drugs Compound 3 and 16 were prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at 5, 24, 48, and 72 hrs post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). Results are shown in the following figures below that depict lowered lymphocyte count after 5 hours (<1 number of lymphocytes $10^3$/µL blood).

What is claimed is:

1. A method of treating an immunosuppressant disorder associated with the sphingosine-1-phosphate receptor inhibition, wherein the disorder is selected from rheumatoid arthritis, psoriasis, atherosclerosis, autoimmune uveitis, dry eye, or multiple sclerosis, in a mammal in need thereof, which comprises administering to a mammal in need thereof, a pharmaceutical composition comprising a therapeutically effective amount of at least one compound represented by Formula I or a pharmaceutically acceptable salt thereof:

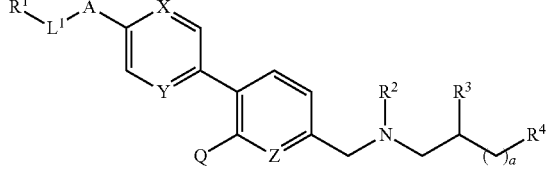

Formula I wherein:
$R^1$ is Me, $CF_3$ or aryl;
$R^2$ is H, $C_{1-10}$ alkyl, or together with $R^3$ forms a 5 or 6 membered heterocycle ring;
$R^3$ is H, $C_{1-10}$ alkyl, or together with $R^2$ forms a 5 or 6 membered heterocycle ring;
$R^4$ is $OPO_3H_2$, carboxylic acid, $C_{1-6}$ alkyl, —$S(O)_2H$, —$P(O)(OH)(OR^{10})$, —$P(O)(H)OH$ or $OR^9$;
X is $CR^5$ or N;
Y is $CR^6$ or N;
Z is $CR^7$ or N;
A is O, $CH_2$ or $NR^8$;
$L^1$ is $C_{2-10}$ alkylene;
$R^5$ is H, $C_{1-10}$ alkyl, $C_{2-6}$ alkenyl or $C_{3-10}$ cycloalkyl;
$R^6$ is H, $C_{1-10}$ alkyl, $C_{2-6}$ alkenyl or $C_{3-10}$ cycloalkyl;
$R^7$ is H, $C_{1-10}$ alkyl, $C_{2-6}$ alkenyl or $C_{3-10}$ cycloalkyl;
$R^8$ is H, $C_{3-10}$ cycloalkyl or $C_{1-6}$ alkyl;
$R^9$ is H or $C_{1-10}$ alkyl;
$R^{10}$ is H or $C_{1-10}$ alkyl;
Q is $C_{3-10}$ cycloalkyl, heterocycle or aryl; and
a is 0, 1, 2, 3 or 4;
in combination with at least one additional component selected from the group consisting of one or more emulsifying agent, wetting agent, sweetening agent, flavoring agent, tonicity adjuster, preservative, buffer, anti-oxidant and combinations thereof.

2. The method according to claim 1, wherein said compound is represented by Formula I wherein:
$R^1$ is Me, $CF_3$, phenyl;
$R^2$ is H, or together with $R^3$ forms a 5 membered heterocycle ring;
$R^3$ is H, or together with $R^2$ forms a 5 membered heterocycle ring;
$R^4$ is —$P(O)(OH)(OR^{10})$;
X is $CR^5$ or N;
Y is $CR^6$ or N;
Z is $CR^7$ or N;
A is O or $CH_2$;
$L^1$ is $C_{2-5}$ alkylene;
$R^5$ is H or $C_{1-6}$ alkyl;
$R^6$ is H;
$R^7$ is H;
$R^{10}$ is H or $C_{1-6}$ alkyl;
Q is heterocycle or aryl; and
a is 0 or 1.

3. The method according to claim 1, wherein said compound is represented by Formula I wherein:
$R^1$ is Me or phenyl;
$R^2$ is H;
$R^3$ is H;
$R^4$ is —$P(O)(OH)(OR^{10})$;
X is $CR^5$;
Y is $CR^6$ or N;
Z is N;
A is $CH_2$;
$L^1$ is $C_{2-5}$ alkylene;
$R^5$ is H or $C_{1-6}$ alkyl;
$R^6$ is H;
$R^{10}$ is H;
Q is heterocycle or aryl; and
a is 1.

4. The method according to claim 1, wherein the compound represented by Formula I is selected from:
(3-{[6-(5-Hexyl-pyridin-2-yl)-biphenyl-3-ylmethyl]-amino}-propyl)-phosphonic acid;
(3-{[6-(6-Hexyl-pyridin-3-yl)-biphenyl-3-ylmethyl]-amino}-propyl)-phosphonic acid;
(3-{[5-(4-Hexyl-phenyl)-6-phenyl-pyridin-2-ylmethyl]-amino}-propyl)-phosphonic acid;
[1-(4-Hexyl-[1,1';2',1'']terphenyl-4'-ylmethyl)-pyrrolidin-3-yl]-phosphonic acid monoethyl ester;
[1-(4-Hexyl-[1,1';2',1'']terphenyl-4'-ylmethyl)-pyrrolidin-3-yl]-phosphonic acid;
(3-{[6-(6-Octyl-pyridin-3-yl)-biphenyl-3-ylmethyl]-amino}-propyl)-phosphonic acid;
(3-{[5-(4-Pentyloxy-phenyl)-6-phenyl-pyridin-2-ylmethyl]-amino}-propyl)-phosphonic acid;
(3-{[6-(4-Fluoro-phenyl)-5-(4-pentyloxy-phenyl)-pyridin-2-ylmethyl]-amino}-propyl)-phosphonic acid;
(3-{[6-(3-Fluoro-phenyl)-5-(4-pentyloxy-phenyl)-pyridin-2-ylmethyl]-amino}-propyl)-phosphonic acid;
(3-{[4-(3-Phenyl-propyl)[1,1';2',1'']terphenyl-4'-ylmethyl]-amino}-propyl)-phosphonic acid;
(3-{[4-(3,3,4,4,5,5,6,6,6-Nonafluoro-hexyl)-[1,1';2',1''] terphenyl-4'-ylmethyl]-amino}-propyl)-phosphonic acid;
(3-{[5-(4-Hexyl-3-propyl-phenyl)-6-phenyl-pyridin-2-ylmethyl]-amino}-propyl)-phosphonic acid;
(3-{[6-(3-Chloro-phenyl)-5-(4-hexyl-3-propyl-phenyl)-pyridin-2-ylmethyl]-amino}-propyl)-phosphonic acid;
[3-({6-Phenyl-5-[4-(3-phenyl-propyl)-phenyl]-pyridin-2-ylmethyl}-amino)-propyl]-phosphonic acid;
[3-({6-(3-Chloro-phenyl)-5-[4-(3-phenyl-propyl)-phenyl]-pyridin-2-ylmethyl}-amino)-propyl]-phosphonic acid;
(3-{[5-(4-Hexyl-phenyl)-6-(3-hydroxy-phenyl)-pyridin-2-ylmethyl]-amino}-propyl)-phosphonic acid;
(3-{[5-(4-Hexyl-phenyl)-6-thiophen-2-yl-pyridin-2-ylmethyl]-amino}-propyl)-phosphonic acid;
(3-{[5-(4-Hexyl-phenyl)-6-thiophen-3-yl-pyridin-2-ylmethyl]-amino}-propyl)-phosphonic acid;
(3-{[6-Furan-2-yl-5-(4-hexyl-phenyl)-pyridin-2-ylmethyl]-amino}-propyl)-phosphonic acid;
(3-{[5-(4-Hexyl-phenyl)-6-oxazol-4-yl-pyridin-2-ylmethyl]-amino}-propyl)-phosphonic acid;
(3-{[5-(4-Hexyl-phenyl)-6-thiazol-2-yl-pyridin-2-ylmethyl]-amino}-propyl)-phosphonic acid;
[3-({5-[4-(3-Phenyl-propyl)-phenyl]-6-thiophen-2-yl-pyridin-2-ylmethyl}-amino)-propyl]-phosphonic acid;
(3-{[5-(4-Hexyl-3-propyl-phenyl)-6-thiophen-2-yl-pyridin-2-ylmethyl]-amino}-propyl)-phosphonic acid;
(3-{[3-(4-Hexyl-phenyl)-[2,3']bipyridinyl-6-ylmethyl]-amino}-propyl)-phosphonic acid; and
(3-{[6-(5-Fluoro-thiophen-2-yl)-5-(4-hexyl-phenyl)-pyridin-2-ylmethyl]-amino}-propyl)-phosphonic acid.

5. The method according to claim 1, wherein the compound represented by Formula I is selected from:
(3-{[5-(4-Hexyl-phenyl)-6-thiophen-2-yl-pyridin-2-ylmethyl]-amino}-propyl)-phosphonic acid
(3-{[6-(5-Fluoro-thiophen-2-yl)-5-(4-hexyl-phenyl)-pyridin-2-ylmethyl]-amino}-propyl)-phosphonic acid,
(3-{[5-(4-Hexyl-3-propyl-phenyl)-6-thiophen-2-yl-pyridin-2-ylmethyl]-amino}-propyl)-phosphonic acid;
[3-({5-[4-(3-Phenyl-propyl)-phenyl]-6-thiophen-2-yl-pyridin-2-ylmethyl}-amino)-propyl]-phosphonic acid;
(3-{[5-(4-Hexyl-phenyl)-6-thiophen-3-yl-pyridin-2-ylmethyl]-amino}-propyl)-phosphonic acid;
(3-{[5-(4-Hexyl-phenyl)-6-oxazol-4-yl-pyridin-2-ylmethyl]-amino}-propyl)-phosphonic acid;
(3-{[6-Furan-2-yl-5-(4-hexyl-phenyl)-pyridin-2-ylmethyl]-amino}-propyl)-phosphonic acid;
[3-({6-Phenyl-5-[4-(3-phenyl-propyl)-phenyl]-pyridin-2-ylmethyl}-amino)-propyl]-phosphonic acid; and (3-{[5-(4-Hexyl-3-propyl-phenyl)-6-phenyl-pyridin-2-yl-methyl]-amino}-propyl)-phosphonic acid.

6. The method according to claim 1, wherein the mammal is a human.

7. The method according to claim 1 in a formulation suitable for oral administration.

8. The method according to claim 1 in a formulation suitable for topical administration.

* * * * *

UNITED STATES PATENT AND TRADEMARK OFFICE
CERTIFICATE OF CORRECTION

PATENT NO.        : 8,513,220 B2
APPLICATION NO.   : 13/569243
DATED             : August 20, 2013
INVENTOR(S)       : Janet A. Takeuchi et al.

It is certified that error appears in the above-identified patent and that said Letters Patent is hereby corrected as shown below:

On the title page, in item (56), under "Other Publications", in column 2, line 1, delete "Sphingosine 1-Phosphate" and insert -- Sphingosine-1-Phosphate --, therefor.

On the title page, in item (56), under "Other Publications", in column 2, line 6, delete "Chemica" and insert -- Chimica --, therefor.

On the title page, in item (56), under "Other Publications", in column 2, line 8, delete "Sterochemistry," and insert -- Stereochemistry, --, therefor.

On the title page, in Primary Examiner, in column 2, line 1, delete "Janet Andreas" and insert -- Janet Andres --, therefor.

In the Specification

In column 1, line 24, delete "Sphingosine-1 phosphate" and insert -- Sphingosine-1-phosphate --, therefor.

In column 1, line 51, delete "theft" and insert -- their --, therefor.

In column 3, line 31, delete "thiopene," and insert -- thiophene, --, therefor.

In column 4, line 15, delete "–P(O)(OH)(O10)," and insert -- –P(O)(OH)(OR10), --, therefor.

In column 4, line 35, delete "thiopene," and insert -- thiophene, --, therefor.

In column 5, line 25, delete "propyl)[" and insert -- propyl)-[ --, therefor.

In column 5, line 56, delete "propylyphosphonic acid." and insert -- propyl)-phosphonic acid. --, therefor.

In column 6, line 34, delete "Stahal& Camille" and insert -- Stahl & Camille --, therefor.

In column 6, line 35, delete "Chemica" and insert -- Chimica --, therefor.

In column 7, line 17, delete "antoimmune" and insert -- autoimmune --, therefor.

In column 8, lines 4-5, delete "antoimmune" and insert -- autoimmune --, therefor.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,513,220 B2

In column 9, line 66, delete "and or" and insert -- and/or --, therefor.

In column 12, line 61, delete "diasteroisomeric" and insert -- diastereoisomeric --, therefor.

In column 13, lines 7-8, delete "Syn Chem," and insert -- SynChem, --, therefor.

In column 14, line 46, delete "1,1',2',1''" and insert -- 1,1':2',1'' --, therefor.

In column 15, line 7, after "3H)" insert -- . --.

In column 15, line 3 (Table 1), delete "1,1': 2',1''-" and insert -- 1,1':2',1''- --, therefor.

In column 15, line 22 (Table 1), delete "1,1': 2',1''-" and insert -- 1,1':2',1''- --, therefor.

In column 15, line 26 (Table 1), delete "1,1': 2',1''-" and insert -- 1,1':2',1''- --, therefor.

In column 16, line 45, after "3H)" insert -- . --.

In column 16, line 67, after "3H)" insert -- . --.

In column 17, line 9, delete "A" and insert -- Å --, therefor.

In column 17, line 20, after "3H)" insert -- . --.

In column 17, line 43, after "acrylaldehyde" insert -- . --.

In column 17, line 48, after "Hz, 3H)" insert -- . --.

In column 18, line 21, after "2H)" insert -- . --.

In column 18, line 36, delete "MgSO4," and insert -- $MgSO_4$, --, therefor.

In columns 23-24, line 72, delete "6H)\" and insert -- 6H) --, therefor.

In column 26, line 43, after "3H)" insert -- . --.

In columns 29-30, line 1 (Interm. No. 51), after "$CDCl_3$)" insert -- δ --.

In column 32, line 41, delete "A" and insert -- Å --, therefor.

In column 49, line 50, delete "dithitothreitol" and insert -- dithiothreitol --, therefor.

In column 49, line 54, delete "adenylylimmidodiphosphate" and insert -- adenylylimidodiphosphate --, therefor.

In column 49, line 62, delete "n-counter." and insert -- β-counter. --, therefor.

In column 52, line 11, delete "(FIGS. 8)" and insert -- (FIG. 8) --, therefor.

In the Claims

In column 54, line 16, in claim 4, delete "propyl)[" and insert -- propyl)-[ --, therefor.

In column 54, line 53, in claim 5, after "acid" insert -- ; --.

In column 54, line 55, in claim 5, delete "acid," and insert -- acid; --, therefor.